(12) United States Patent
Siddique et al.

(10) Patent No.: US 9,173,897 B2
(45) Date of Patent: Nov. 3, 2015

(54) MOLECULAR TARGETS FOR ALS AND RELATED DISORDERS

(75) Inventors: Teepu Siddique, Chicago, IL (US); Wenjie Chen, Chicago, IL (US); Han-Xiang Deng, Chicago, IL (US); Yi Yang, Chicago, IL (US)

(73) Assignee: NORTHWESTERN UNIVERSITY, Evanston, IL (US)

( * ) Notice: Subject to any disclaimer, the term of this patent is extended or adjusted under 35 U.S.C. 154(b) by 565 days.

(21) Appl. No.: 13/313,884

(22) Filed: Dec. 7, 2011

(65) Prior Publication Data

US 2012/0141459 A1 Jun. 7, 2012

Related U.S. Application Data

(60) Provisional application No. 61/420,530, filed on Dec. 7, 2010.

(51) Int. Cl.
*C12Q 1/68* (2006.01)
*C12P 19/34* (2006.01)
*A61K 31/713* (2006.01)

(52) U.S. Cl.
CPC ............ *A61K 31/713* (2013.01); *C12Q 1/6883* (2013.01); *C12Q 2600/156* (2013.01); *G01N 2800/28* (2013.01); *G01N 2800/50* (2013.01)

(58) Field of Classification Search
CPC ........... C12Q 1/6883; C12Q 2600/156; G01N 2800/28
See application file for complete search history.

(56) References Cited

U.S. PATENT DOCUMENTS

| | | | |
|---|---|---|---|
| 5,538,848 | A | 7/1996 | Livak et al. |
| 5,639,606 | A | 6/1997 | Willey |
| 5,643,765 | A | 7/1997 | Willey |
| 5,692,233 | A | 11/1997 | Garman |
| 5,876,978 | A | 3/1999 | Willey et al. |

OTHER PUBLICATIONS

Juppner; Bone, vol. 17; 1995, pp. 39S-40S.*
Lucentini (The Scientist; 2004, vol. 24, p. 20).*
Hegele (Arterioscler. Thromb. Vasc. Biol.; 2002, vol. 22, pp. 1058-1061).*
Aguzzi et al. "Protein aggregation diseases: pathogenicity and therapeutic perspectives," Nat Rev Drug Discov, 9 (3): 237-248, 2010.
Bertram et al. "Family-based association between Alzheimer's disease and variants in UBQLN1," New Engl J Med, 352(9): 884-894, 2005.
Brooks et al. "El Escorial revisited: revised criteria for the diagnosis of amyotrophic lateral sclerosis," Amyotroph Lateral Scler Other Motor Neuron Disord, 1(5): 293-299, 2000.
Chen et al. "DNA/RNA helicase gene mutamastions in a form of juvenile amyotrophic lateral sclerosis (ALS4)," Am J Hum Genet, 74(6): 1128-1135, 2004.
Chow et al. "Deleterious variants of FIG4, a phosphoinositide phosphatase, in patients with ALS," Am J Hum Genet, 84(1): 85-88, 2009.
Dantuma et al. "Short-lived green fluorescent proteins for quantifying ubiquitin/proteasome-dependent proteolysis in living cells," Nat Biotechnol, 18(5): 538-543, 2000.
Deng et al. "Amyotrophic lateral sclerosis and structural defects in Cu,Zn superoxide dismutase," Science, 261 (5124):1047-1051, 1993.
Deng et al. "Conversion to the amyotrophic lateral sclerosis phenotype is associated with intermolecular linked insoluble aggregates of SOD1 in mitochondria," Proc Natl Acad Sci USA, 103(18): 7142-7147, 2006.
Deng et al. "FUS-immunoreactive inclusions are a common feature in sporadic and non-SOD1 familial amyotrophic lateral sclerosis," Ann Neurol, 67(6): 739-748, 2010.
Deng et al. "Mutations in UBQLN2 cause dominant X-linked juvenile and adult-onset ALS and ALS/dementia," Nature, 477(7363): 211-215, 2011.
Greenway et al. "ANG mutations segregate with familial and 'sporadic' amyotrophic lateral sclerosis," Nat Genet, 38 (4): 411-413, 2006.
Hernandez et al. "Testing the ubiquitin-proteasome hypothesis of neurodegeneration in vivo," Trends Neurosci, 27 (2): 66-69, 2004.
Kabashi et al. "TARDBP mutations in individuals with sporadic and familial amyotrophic lateral sclerosis," Nat Genet, 40(5): 572-574, 2008.
Kim et al. "Potentiation of amyotrophic lateral sclerosis (ALS)-associated TDP-43 aggregation by the proteasome-targeting factor, ubiquilin 1," J Biol Chem, 284(12): 8083-8092, 2009.
Kwiatkowski et al. "Mutations in the FUS/TLS gene on chromosome 16 cause familial amyotrophic lateral sclerosis," Science, 323(5918): 1205-1208, 2009.
Lansbury et al. "A century-old debate on protein aggregation and neurodegeneration enters the clinic," Nature, 443 (7113): 774-779, 2006.
Leigh et al. "Ubiquitin-immunoreactive intraneuronal inclusions in amyotrophic lateral sclerosis. Morphology, distribution, and specificity," Brain, 114(Pt 2): 775-788, 1991.
Leroy et al. "The ubiquitin pathway in Parkinson's disease," Nature, 395(6701): 451-452, 1998.
Lowe et al. "New pathological findings in amyotrophic lateral sclerosis," J Neurol Sci, 124 Suppl:38-51, 1994.
Mackenzie et al. "Pathological TDP-43 distinguishes sporadic amyotrophic lateral sclerosis from amyotrophic lateral sclerosis with SOD1 mutations," Ann Neurol, 61(5): 427-434, 2007.
Maruyama et al. "Mutations of optineurin in amyotrophic lateral sclerosis," Nature, 465(7295): 223-226, 2010.
Massey et al. "Overexpression of ubiquilin decreases ubiquitination and degradation of presenilin proteins," J Alzheimers Dis, 6(1): 79-92, 2004.
Mitchell et al. "Familial amyotrophic lateral sclerosis is associated with a mutation in D-amino acid oxidase," Proc Natl Acad Sci USA, 107(16): 7556-7561, 2010.

(Continued)

*Primary Examiner* — Jehanne Sitton
(74) *Attorney, Agent, or Firm* — Foley & Lardner LLP

(57) ABSTRACT

Provided herein are compositions and methods for diagnosis, risk assessment, research, and therapy related to amyotrophic lateral sclerosis (ALS) and ALS-related disorders. In particular, the present invention relates to mutations in the UBQLN2 gene that cause dominantly inherited chromosome X-linked ALS and ALS/dementia.

4 Claims, 18 Drawing Sheets

(56) References Cited

OTHER PUBLICATIONS

N'Diaye et al. "The ubiquitin-like protein PLIC-2 is a negative regulator of G protein-coupled receptor endocytosis," Mol Biol Cell, 19(3): 1252-1260, 2008.

Neary et al. "Frontotemporal lobar degeneration: a consensus on clinical diagnostic criteria," Neurology, 51(6): 1546-1554, 1998.

Neumann et al. "Ubiquitinated TDP-43 in frontotemporal lobar degeneration and amyotrophic lateral sclerosis," Science, 314(5796): 130-133, 2006.

Nishimura et al. "A mutation in the vesicle-trafficking protein VAPB causes late-onset spinal muscular atrophy and amyotrophic lateral sclerosis," Am J Hum Genet, 75(5): 822-831, 2004.

Rosen et al. "Mutations in Cu/Zn superoxide dismutase gene are associated with familial amyotrophic lateral sclerosis," Nature, 362(6415): 59-62, 1993.

Rothenberg et al. "Ubiquitin at a crossroads in protein degradation pathways," Autophagy, 6(7): 979-980, 2010.

Schrader et al. "Targeting proteins for degradation," Nat Chem Biol, 5(11): 815-822, 2009.

Shibata et al. "Intense superoxide dismutase-1 immunoreactivity in intracytoplasmic hyaline inclusions of familial amyotrophic lateral sclerosis with posterior column involvement," J Neuropathol Exp Neurol, 55(4): 481-490, 1996.

Shibata et al. "Presence of Cu/Zn superoxide dismutase (SOD) immunoreactivity in neuronal hyaline inclusions in spinal cords from mice carrying a transgene for Gly93Ala mutant human Cu/Zn SOD," Acta Neuropathol, 95(2): 136-142, 1998.

Shimura et al. "Familial Parkinson disease gene product, parkin, is a ubiquitin-protein ligase," Nat Genet, 25(3): 302-305, 2000.

Sreedharan et al. "TDP-43 mutations in familial and sporadic amyotrophic lateral sclerosis," Science, 319(5870): 1668-1672, 2008.

Strausberg et al. "Homo sapiens ubiquilin 2, mRNA (cDNA clone MGC:78469 IMAGE: 4543266), complete cds," GenBank Accession No. BC069237.1, as retrieved on Mar. 22, 2012 from <http://www.ncbi.nlm.nih.gov.ezp-prod1.hul.harvard.edu/nuccore/BC069237.1.

Su et al. "Ubiquitin-like and ubiquitin-associated domain proteins: significance in proteasomal degradation," Cell Mol Life Sci, 66(17): 2819-2833, 2009.

Su et al., "Homo sapiens ubiquilin 4 (UBQLN4), mRNA," GenBank Accession No. NM_02131.3, as accessed on Sep. 12, 2012 from <www.ncbi.nlm.nih.gov/nuccore/NM_020131.3>.

Ticozzi et al. "Paraoxonase gene mutations in amyotrophic lateral sclerosis," Ann Neurol, 68(1): 102-107, 2010.

Van Deerlin et al. "TARDBP mutations in amyotrophic lateral sclerosis with TDP-43 neuropathology: a genetic and histopathological analysis," Lancet Neurol, 7(5): 409-416, 2008.

Vance et al. "Mutations in FUS, an RNA processing protein, cause familial amyotrophic lateral sclerosis type 6," Science, 323(5918): 1208-1211, 2009.

Yang et al. "The gene encoding alsin, a protein with three guanine-nucleotide exchange factor domains, is mutated in a form of recessive amyotrophic lateral sclerosis," Nat Genet, 29(2):160-165, 2001.

International Search Report and Written Opinion for Int'l Application No. PCT/US2011/063788, mailed Apr. 4, 2012.

* cited by examiner

FIG. 2F

| | | P497H<br>P497S | P506T P506T | P525S | | |
|---|---|---|---|---|---|---|
| Human | GVLGTAIGPVGPVTPIGPIGPIVPFTPIGPIGPIGPTGPAAPPGSTGSGG | 532 | SEQ ID NO.: 7 |
| Chimpanzee | GVLGTAIGPVGPVTPIGPIGPIVPFTPIGPIGPIGPTGPAGPPGSTGSGG | 532 | SEQ ID NO.: 8 |
| Dog | GVLGTAIGPVGPVTPIGPIGPIVPFTPIGPIGPIGPTGPAG-PGSTGSGG | 531 | SEQ ID NO.: 9 |
| Cattle | GVLGTAIGPVGPVTPIGPIGPIVPFTPIGPIGPIGPTGPAGPPGSTGTGA | 532 | SEQ ID NO.: 10 |
| Mouse | GVLGTAITPVGPVTPIGPIGPIVPFTPIGPIGPIGPTGPASSPGSTGTGI | 546 | SEQ ID NO.: 11 |
| Rat | GVLGTAITPVGPVTPIGPIGPIVPFTPIGPIGPIGPTGPASSPGSTGTGI | 546 | SEQ ID NO.: 12 | ns

SEQUENCE LISTING

```
<160> NUMBER OF SEQ ID NOS: 12

<210> SEQ ID NO 1
<211> LENGTH: 27
<212> TYPE: DNA
<213> ORGANISM: Artificial Sequence
<220> FEATURE:
<223> OTHER INFORMATION: Synthetic

<400> SEQUENCE: 1
ttctcgaggg ccgccatggc tgagaat                                27

<210> SEQ ID NO 2
<211> LENGTH: 26
<212> TYPE: DNA
<213> ORGANISM: Artificial Sequence
<220> FEATURE:
<223> OTHER INFORMATION: Synthetic

<400> SEQUENCE: 2
catggatcct gtatgtctgt attacc                                 26

<210> SEQ ID NO 3
<211> LENGTH: 11
<212> TYPE: DNA
<213> ORGANISM: Homo sapien

<400> SEQUENCE: 3
cacccccata g                                                 11

<210> SEQ ID NO 4
<211> LENGTH: 11
<212> TYPE: DNA
<213> ORGANISM: Homo sapien

<400> SEQUENCE: 4
tagtcccttt t                                                 11

<210> SEQ ID NO 5
<211> LENGTH: 11
<212> TYPE: DNA
<213> ORGANISM: Homo sapien

<400> SEQUENCE: 5
ttacccccat a                                                 11
```

-continued

<210> SEQ ID NO 6
<211> LENGTH: 11
<212> TYPE: DNA
<213> ORGANISM: Homo sapien

<400> SEQUENCE: 6 cccccctgg c                                                                  11

<210> SEQ ID NO 7
<211> LENGTH: 50
<212> TYPE: PRT
<213> ORGANISM: Homo sapien

<400> SEQUENCE: 7

Gly Val Leu Gly Thr Ala Ile Gly Pro Val Gly Pro Val Thr Pro Ile
1               5                   10                  15

Gly Pro Ile Gly Pro Ile Val Pro Phe Thr Pro Ile Gly Pro Ile Gly
            20                  25                  30

Pro Ile Gly Pro Thr Gly Pro Ala Ala Pro Pro Gly Ser Thr Gly Ser
        35                  40                  45

Gly Gly
    50

<210> SEQ ID NO 8
<211> LENGTH: 50
<212> TYPE: PRT
<213> ORGANISM: P. troglodytes

<400> SEQUENCE: 8

Gly Val Leu Gly Thr Ala Ile Gly Pro Val Gly Pro Val Thr Pro Ile
1               5                   10                  15

Gly Pro Ile Gly Pro Ile Val Pro Phe Thr Pro Ile Gly Pro Ile Gly
            20                  25                  30

Pro Ile Gly Pro Thr Gly Pro Ala Gly Pro Pro Gly Ser Thr Gly Ser
        35                  40                  45

Gly Gly
    50

<210> SEQ ID NO 9
<211> LENGTH: 49
<212> TYPE: PRT
<213> ORGANISM: C. lupus familiaris

<400> SEQUENCE: 9

Gly Val Leu Gly Thr Ala Ile Gly Pro Val Gly Pro Val Thr Pro Ile
1               5                   10                  15

Gly Pro Ile Gly Pro Ile Val Pro Phe Thr Pro Ile Gly Pro Ile Gly
            20                  25                  30

Pro Ile Gly Pro Thr Gly Pro Ala Gly Pro Gly Ser Thr Gly Ser Gly
        35                  40                  45

Gly

<210> SEQ ID NO 10
<211> LENGTH: 50
<212> TYPE: PRT
<213> ORGANISM: B. taurus

<400> SEQUENCE: 10

Gly Val Leu Gly Thr Ala Ile Gly Pro Val Gly Pro Val Thr Pro Ile
1               5                   10                  15

```
Gly Pro Ile Gly Pro Ile Val Pro Phe Thr Pro Ile Gly Pro Ile Gly
            20                  25                  30

Pro Ile Gly Pro Thr Gly Pro Ala Gly Pro Pro Gly Ser Thr Gly Thr
        35                  40                  45

Gly Ala
    50

<210> SEQ ID NO 11
<211> LENGTH: 50
<212> TYPE: PRT
<213> ORGANISM: M. musculus

<400> SEQUENCE: 11

Gly Val Leu Gly Thr Ala Ile Thr Pro Val Gly Pro Val Thr Pro Ile
1               5                   10                  15

Gly Pro Ile Gly Pro Ile Val Pro Phe Thr Pro Ile Gly Pro Ile Gly
            20                  25                  30

Pro Ile Gly Pro Thr Gly Pro Ala Ser Ser Pro Gly Ser Thr Gly Thr
        35                  40                  45

Gly Ile
    50

<210> SEQ ID NO 12
<211> LENGTH: 50
<212> TYPE: PRT
<213> ORGANISM: R. norvegicus

<400> SEQUENCE: 12

Gly Val Leu Gly Thr Ala Ile Thr Pro Val Gly Pro Val Thr Pro Ile
1               5                   10                  15

Gly Pro Ile Gly Pro Ile Val Pro Phe Thr Pro Ile Gly Pro Ile Gly
            20                  25                  30

Pro Ile Gly Pro Thr Gly Pro Ala Ser Ser Pro Gly Ser Thr Gly Thr
        35                  40                  45

Gly Ile
    50
```

MOLECULAR TARGETS FOR ALS AND RELATED DISORDERS

CROSS-REFERENCE TO RELATED APPLICATION

The present invention claims priority to U.S. Provisional Patent Application Ser. No. 61/420,530 filed Dec. 7, 2010, which is hereby incorporated by reference in its entirety.

FIELD OF THE INVENTION

Provided herein are compositions and methods for diagnosis, risk assessment, research, and therapy related to amyotrophic lateral sclerosis (ALS) and ALS-related disorders. In particular, the present invention relates to mutations in the UBQLN genes (e.g., UBQLN2 and UBQLN4) that cause dominantly inherited chromosome X-linked ALS and ALS/dementia.

BACKGROUND

Amyotrophic lateral sclerosis (ALS) is a paralytic disorder characterized by degeneration of motor neurons in the brain and spinal cord. Though most cases of ALS are sporadic, about 5-10% occur in familial clusters. Mutations in superoxide dismutase 1 (SOD1) (1, 2), (TAR) DNA-binding protein TDP-43 (3-5) and fused in sarcoma/translated in liposarcoma (FUS/TLS) (6, 7) represent the causes for significant fractions of classic familial ALS. Mutations in several other genes have also been reported to cause ALS or ALS-like syndromes (8-15). Altogether, mutations in the known genes account for approximately 30% of familial ALS cases, but causes for the other forms of familial ALS and the vast majority of sporadic ALS are unknown. The central pathogenic mechanism underlying motor neuron degeneration in ALS remains to be understood.

SUMMARY OF THE INVENTION

Embodiments of the present disclosure provide methods for detecting the presence or absence of one or more mutations in a UBIQLN gene (e.g., UBQLN2 and UBQLN4) mutation in a subject. In some embodiments, a subject is characterized as suffering from ALS based on the presence of one or more mutations in UBIQLN genes (e.g., UBQLN2 and UBQLN4). In some embodiments, a subject is characterized as being at increased risk of developing ALS based on the presence of one or more mutations in UBIQLN genes (e.g., UBQLN2 and UBQLN4). In some embodiments, compositions and methods are provided for detecting one or more mutations in the UBQLN2 gene, including c.1490C>A, c.1489C>T, c.1516C>A, c.1525C>T, and c.1573C>T. In some embodiments, compositions and methods are provided for detecting one or more mutations in the UBQLN4 gene, including 202A>C (of NCBI Reference Sequence: NM_020131.3).

Embodiments of the present disclosure provide methods for identifying a subject suffering from ALS and/or a related disorder, comprising: exposing a patient sample (e.g., cell, or a secretion thereof) to a detection reagent; and detecting the presence in the sample of mutations in a UBQLN gene (e.g., UBQLN2 gene, UBQLN4 gene, etc.) or Ubiquilin protein (e.g., Ubiquilin2, Ubiquilin4, etc.). Embodiments of the present disclosure provide methods for identifying a subject at risk of developing ALS and/or a related disorder, comprising: exposing a patient sample (e.g., cell, or a secretion thereof) to a detection reagent; and detecting the presence or absence in the sample of mutations in a UBQLN gene (e.g., UBQLN2 gene, UBQLN4 gene, etc.) or Ubiquilin protein (e.g., Ubiquilin2, Ubiquilin4, etc.). Detection of mutations is performed at the nucleic acid or protein levels, by methods understood to those in the field. Further embodiments provide the step of determining a treatment course of action based on the presence or absence of a mutant UBQLN gene (e.g., mutant UBQLN2 gene, mutant UBQLN4 gene, etc.) or mutant Ubiquilin protein (e.g., mutant Ubiquilin2, mutant Ubiquilin4, etc.).

Embodiments of the present invention provide methods for treatment and/or prevention of ALS and/or ALS-related disorders by targeting mutations in a UBQLN gene (e.g., UBQLN2 gene, UBQLN4 gene, etc.) or Ubiquilin protein (e.g., Ubiquilin2, Ubiquilin4, etc.), or the downstream products thereof (e.g. proteins, pathways, etc.). In some embodiments, the present invention provides compositions for treatment and/or prevention of ALS and/or ALS-related disorders. In some embodiments, the present invention provides compositions (e.g. proteins (e.g. antibodies, replacement proteins, etc.), small molecules (e.g. pharmaceuticals), nucleic acids (e.g. siRNA, miRNA, gene therapy, etc.), etc.) that target mutations in a UBQLN gene (e.g., UBQLN2 gene, UBQLN4 gene, etc.) or Ubiquilin protein (e.g., Ubiquilin2, Ubiquilin4, etc.), or the downstream products thereof (e.g. proteins, pathways, etc.). In some embodiments, the present invention provides compositions that inhibit expression of mutant UBQLN genes (e.g., UBQLN2 gene, UBQLN4 gene, etc.) or suppress the function of a Ubiquilin protein (e.g., Ubiquilin2, Ubiquilin4, etc.) or the downstream products thereof (e.g. proteins, pathways, etc.). In some embodiments, the present invention provides compositions that replace the aberrant function of mutant UBQLN genes (e.g., UBQLN2 gene, UBQLN4 gene, etc.) or Ubiquilin protein (e.g., Ubiquilin2, Ubiquilin4, etc.), or downstream products thereof (e.g. proteins, pathways, etc.).

Embodiments of the present invention provide compositions, methods, and assays for screening therapeutics (e.g. proteins (e.g. antibodies, replacement proteins, etc.), small molecules (e.g. pharmaceuticals), nucleic acids (e.g. siRNA, miRNA, gene therapy, etc.), etc.) to treat and/or prevent ALS and/or ALS-related disorders. In some embodiments, compositions are screened for effectiveness in treating and/or preventing ALS and/or ALS-related disorders based on their affinity to, suppression of, or replacement of mutant UBQLN gene (e.g., UBQLN2 gene, UBQLN4 gene, etc.) or mutant Ubiquilin protein (e.g., Ubiquilin2, Ubiquilin4, etc.), or downstream products thereof (e.g. proteins, pathways, etc.).

The mutant UBQLN genes (e.g., UBQLN2 gene, UBQLN4 gene, etc.) and/or mutant Ubiquilin protein (e.g., Ubiquilin2, Ubiquilin4, etc.) of the present disclosure, including fragments, derivatives and analogs thereof, may be used as immunogens to produce antibodies having use in the diagnostic, screening, research, and therapeutic methods. The antibodies may be polyclonal or monoclonal, chimeric, humanized, single chain, Fv or Fab fragments. Various procedures known to those of ordinary skill in the art may be used for the production and labeling of such antibodies and fragments. See, e.g., Burns, ed., *Immunochemical Protocols, 3rd ed.*, Humana Press (2005); Harlow and Lane, *Antibodies: A Laboratory Manual*, Cold Spring Harbor Laboratory (1988); Kozbor et al., Immunology Today 4: 72 (1983); Köhler and Milstein, Nature 256: 495 (1975). Antibodies or fragments exploiting the differences between mutant UBQLN genes (e.g., UBQLN2 gene, UBQLN4 gene, etc.) and/or mutant Ubiquilin protein (e.g., Ubiquilin2, Ubiquilin4, etc.) and their wild-type counterparts are provided.

The present disclosure provides DNA, RNA and protein based diagnostic and screening methods that either directly or indirectly detect mutant UBQLN genes (e.g., UBQLN2 gene, UBQLN4 gene, etc.) and/or mutant Ubiquilin protein (e.g., Ubiquilin2, Ubiquilin4, etc.). The present disclosure also provides compositions and kits for diagnostic and screening purposes In some embodiments, kit comprise reagents configured to detect mutant UBQLN genes (e.g., UBQLN2 gene, UBQLN4 gene, etc.) and/or mutant Ubiquilin protein (e.g., Ubiquilin2, Ubiquilin4, etc.). In some embodiments, the diagnostic and screening methods may be qualitative or quantitative. In some embodiments, the diagnostic and screening methods may be conducted in vitro or in vivo. In some embodiments, the diagnostic and screening methods may comprise nucleic acid detection involving, for example: DNA amplification (e.g. PCR), sequencing, hybridization techniques (e.g. In situ hybridization), etc. In some embodiments, the diagnostic and screening methods may comprise protein detection involving, for example: protein sequencing, immunoassays (e.g., Western blot, ELISA, immunohistochemisty, etc.), flow cytometry, mass spectrometry, etc. In some embodiments, high through-put molecular screening techniques are provided to identify compositions targeting mutant UBQLN genes (e.g., UBQLN2 gene, UBQLN4 gene, etc.) and/or mutant Ubiquilin protein (e.g., Ubiquilin2, Ubiquilin4, etc.). In some embodiments, detection of mutant UBQLN genes (e.g., UBQLN2 gene, UBQLN4 gene, etc.) and/or mutant Ubiquilin protein (e.g., Ubiquilin2, Ubiquilin4, etc.) is provided by in vivo imaging techniques, including but not limited to: radionuclide imaging; positron emission tomography (PET); computerized axial tomography, X-ray or magnetic resonance imaging methods, fluorescence detection, and chemiluminescent detection.

The present disclosure contemplates the generation of transgenic animals comprising mutant UBQLN genes (e.g., UBQLN2 gene, UBQLN4 gene, etc.) or mutants and variants thereof (e.g., truncations or single nucleotide polymorphisms). In preferred embodiments, the transgenic animal displays an altered phenotype (e.g., increased or decreased presence ALS and/or ALS-related disorders) as compared to wild-type animals. Methods for analyzing the presence or absence of such phenotypes are provided.

Any of these compositions, alone or in combination with other compositions of the present disclosure, may be provided in the form of a kit.

In some embodiments, the present invention provides a method for characterizing a subject's risk for developing ALS, or identifying a subject as suffering from ALS, comprising detecting the presence of or the absence of one or more mutations on or near one or more UBQLN genes (e.g., UBQLN2, UBQLN4, etc.). In some embodiments, the mutations occur alone or in combination with other markers (e.g. known markers). In some embodiments, mutations are identified in the UBQLN2 gene, including c.1490C>A, c.1489C>T, c.1516C>A, c.1525C>T, and c.1573C>T. In some embodiments, mutations are identified in the UBQLN4 gene, including 202A>C (of NCBI Reference Sequence: NM_020131.3). In some embodiments, mutations described herein are detected in combination with other markers (e.g. known markers) of ALS. In some embodiments, methods comprise detecting the presence of or the absence of two or more mutations indicative of ALS. In some embodiments, methods comprise detecting the presence of or the absence of five or more mutations indicative of ALS. In some embodiments, detection of one or more UBQLN2 and/or UBQLN4 mutations (e.g. 1, 2, 3, 4, 5, 6, or more) indicates an elevated risk of developing ALS. In some embodiments, detection of one or more UBQLN2 and/or UBQLN4 mutations (e.g. 1, 2, 3, 4, 5, 6, or more) indicates a subject suffers from ALS.

In some embodiments, the present invention provides a panel of ALS markers (e.g., mutations in UBQLN2 and/or UBQLN4). In some embodiments, the present invention comprises a panel of two or more ALS markers. In some embodiments, the present invention comprises a panel of three or more ALS markers. In some embodiments, the present invention comprises a panel of four or more ALS markers. In some embodiments, the present invention comprises a panel of five or more ALS markers.

In some embodiments, the present invention provides methods for identifying a subject at risk of developing ALS and/or ALS-related disorders, comprising: (a) exposing a patient sample to a detection reagent; and (b) detecting the presence or absence in the patient sample of one or more mutations in the UBQLN2 gene, wherein detecting the presence in the sample of mutations in the UBQLN2 gene is indicative of an increased risk of developing ALS and/or ALS-related disorders in the patient. In some embodiments, the patient sample comprises a cell, secretion, blood, or fraction thereof. In some embodiments, the mutations are selected from: c.1490C>A, c.1489C>T, c.1516C>A, c.1525C>T, and c.1573C>T. In some embodiments, detecting the presence in the sample of mutations in the UBQLN2 gene indicates that the patient suffers from ALS. In some embodiments, detecting the presence in the sample of mutations in the UBQLN2 gene indicates the patient that served as the source of the sample will develop ALS and/or ALS-related disorder.

In some embodiments, the present invention provides methods for identifying compositions effective in treating or preventing ALS and/or ALS-related disorders, comprising: identifying compositions capable of inhibiting, suppressing, and/or replacing the lost function caused by mutations in the UBQLN2 gene. In some embodiments, the mutations are selected from: c.1490C>A, c.1489C>T, c.1516C>A, c.1525C>T, and c.1573C>T. In some embodiments, the present invention provides a composition effective in treating or preventing ALS and/or ALS-related disorders.

In some embodiments, the present invention provides methods for identifying a subject at risk of developing ALS and/or ALS-related disorders, comprising: (a) exposing a patient sample to a detection reagent; and (b) detecting the presence or absence in the patient sample of one or more mutations in the UBQLN4 gene, wherein detecting the presence in the sample of mutations in the UBQLN4 gene is indicative of an increased risk of developing ALS and/or ALS-related disorders in the patient. In some embodiments, patient sample comprises a cell, secretion, blood, or fraction thereof. In some embodiments, mutations comprise 202A>C. In some embodiments, detecting the presence in the sample of mutations in the UBQLN4 gene indicates that the patient suffers from ALS. In some embodiments, detecting the presence in the sample of mutations in the UBQLN4 gene indicates the patient that served as the source of the sample will develop ALS and/or ALS-related disorder.

In some embodiments, the present invention provides methods for identifying compositions effective in treating or preventing ALS and/or ALS-related disorders, comprising: identifying compositions capable of inhibiting, suppressing, and/or replacing the lost function caused by mutations in the UBQLN4 gene. In some embodiments, the mutations comprise 202A>C. In some embodiments, the present invention provides a composition effective in treating or preventing ALS and/or ALS-related disorders.

DEFINITIONS

Figure 1:
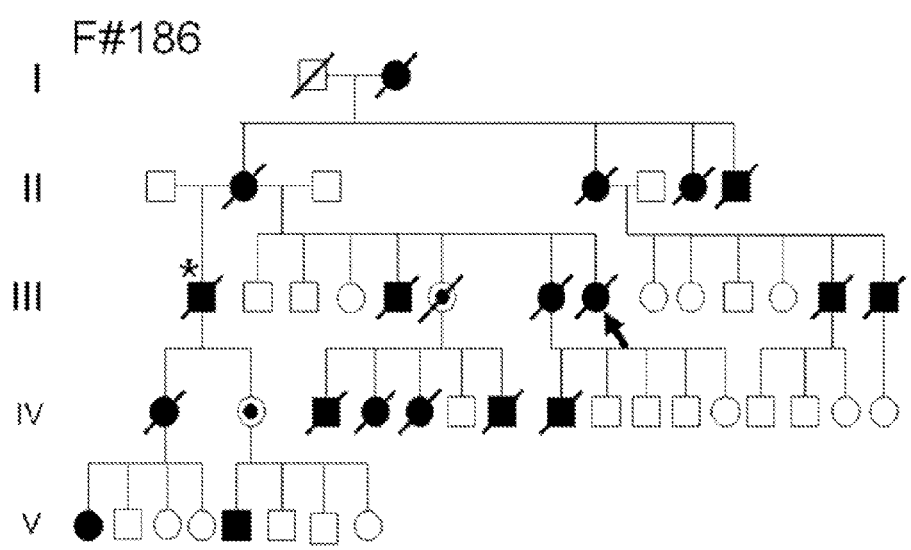
FIG. 1 shows a simplified pedigree of a family with ALS (F#186). The entire pedigree has 119 individuals. The filled square and circle indicate affected male and female, respectively. The arrow indicates proband. An ALS patient (III1) with dementia is indicated with an asterisk.

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

As used herein, the term "subject suspected of having ALS" refers to a subject that presents one or more symptoms indicative of ALS, has one or more risk factors for ALS, or is being screened for ALS (e.g., during a routine physical). A subject suspected of having ALS has generally not been tested for ALS, or has not had a recent test which indicated the subject suffers from ALS. However, a "subject suspected of having ALS" encompasses an individual who has received a preliminary diagnosis but for whom a confirmatory test has not been done. A "subject suspected of having ALS" is sometimes diagnosed with ALS and is sometimes found to not have ALS.

As used herein, the term "subject diagnosed with ALS" refers to a subject who has been tested and found to have ALS. ALS may be diagnosed using any suitable method, including but not limited to, the diagnostic methods of the present invention.

As used herein, the term "subject suffering from ALS" refers to a subject who has ALS and exhibits one or more symptoms thereof. A subject suffering from ALS may or may not have received a diagnosis, and may or may not be aware of the condition.

As used herein, the term "initial diagnosis" refers to a test result of initial ALS diagnosis that reveals the presence or absence or risk of ALS. An initial diagnosis does not include information about the stage or extent of ALS.

As used herein, the term "subject at risk for ALS" refers to a subject with one or more risk factors for developing ALS. Risk factors include, but are not limited to genetic predisposition (e.g., presence of UBQLN2 and/or UBQLN4 mutations).

As used herein, the term "characterizing ALS in subject" refers to the identification of one or more properties of ALS in a subject (e.g. degree, severity, advancement, etc.). ALS may be characterized by the identification of one or more markers (e.g., mutations) of the present invention.

As used herein, the term "reagent(s) capable of specifically detecting biomarker expression" refers to reagents used to detect the expression of biomarkers (e.g., mutations). Examples of suitable reagents include but are not limited to, nucleic acid probes capable of specifically hybridizing to mRNA or cDNA, and antibodies (e.g., monoclonal antibodies).

DETAILED DESCRIPTION OF THE INVENTION

The present invention relates generally to biomarkers for neurodegenerative diseases and disorders (e.g., ALS). Although embodiments of the invention are described in conjunction with ALS, it should be understood that in some embodiments, the biomarkers provided (e.g., UBQLN2 and UBQLN4) herein find use in diagnosis, treatment, and drug screening for other neurodegenerative disorders, including, but not limited to: frontotemporal dementia, dementia with Lewy bodies, corticobasal degeneration, progressive supranuclear palsy, prion disorders, Huntington's disease, multiple system atrophy, amyotrophic lateral sclerosis, hereditary spastic paraparesis, spinocerebellar atrophies, Friedreich's ataxia, amyloidoses, multiple sclerosis, and Charcot Marie Tooth. In some embodiments, the present invention provides biomarkers for ALS. Provided herein are molecular targets for: therapies, therapeutic screening, and risk assessment of Amyotrophic lateral sclerosis (ALS) and ALS-related disorders. Provided herein are mutations in the UBQLN genes (e.g. UBQLN2, UBQLN4, etc.) that cause dominantly inherited chromosome X-linked ALS and ALS/dementia, and provides: therapies, therapeutic screening, and assessment of subject's risk for ALS, based thereon. In particular, provided herein are mutations in UBQLN2 (e.g., 1490C>A, c.1489C>T, c.1516C>A, c.1525C>T, and c.1573C>T) and/or UBQLN4 (e.g., 202A>C of NCBI Reference Sequence: NM_020131.3). In some embodiments, the compositions and methods are provided for detecting mutations in UBQLN2 (e.g., 1490C>A, c.1489C>T, c.1516C>A, c.1525C>T, and c.1573C>T) and/or UBQLN4 (e.g., 202A>C of NCBI Reference Sequence: NM_020131.3) in a subject. In some embodiments, a subject is identified as being at risk for, or suffering from, ALS or an ALS-related disorder based on detection of one or more mutations in UBQLN genes (e.g. UBQLN2, UBQLN4, etc.). In some embodiments, the present invention provides a method for characterizing a subject's risk for developing ALS comprising detecting the presence of or the absence of one or more mutations on or near one or more UBQLN genes (e.g., UBQLN2, UBQLN4, etc.). In some embodiments, the mutations occur alone or in combination with other markers (e.g. known markers).

Accordingly, in some embodiments, the present invention provides methods for detection of ALS, characterizing the severity and/or advancement of ALS, and/or diagnosing a subject's susceptibility for developing ALS. In some embodiments, the present invention detects the presence of one or more of the mutations described herein.

The present invention is not limited by the method utilized for detection. Indeed, a variety of different methods are known to those of skill in the art including, but not limited to, microarray detection, TAQMAN, PCR, allele specific PCR, sequencing, and other methods.

In some embodiments, the present invention provides indicators (e.g. genes, mutations, etc.) of ALS, and/or of increased susceptibility to ALS for an individual or population. In some embodiments, a single indicator (e.g. UBIQLN2 or UBIQLN4 mutation) indicates an increased ALS-susceptibility or the presence of ALS. In some embodiments, a combination of any of the UBQLN mutations described herein indicates heightened risk of having or developing ALS. In some embodiments, combinations of the mutations described herein indicate heightened risk of having ALS or developing ALS. In some embodiments, specific combinations of the UBIQLN mutations described herein indicate increased risk of ALS or developing ALS. In some embodiments, combinations of the UBIQLN mutations described herein indicate increased severity of ALS. In some embodiments, increased number of the UBIQLN mutations described herein indicates increased severity of ALS. In some embodiments, specific combinations of the UBIQLN mutations described herein indicate increased severity of ALS. In some embodiments, a greater number of the UBIQLN mutations described herein which are indicative of ALS correlates to a greater risk of ALS for an individual or population.

Experiments conducted during development of embodiments of the present invention demonstrate that mutations in the UBQLN2 gene cause dominantly inherited chromosome X-linked ALS and ALS/dementia. The UBQLN2 encodes a ubiquitin-like protein, Ubiquilin2, which functionally links the ubiquitination machinery to the proteasome and affects protein degradation. Ubiquilin2 was present in uniquitin-positive inclusions in the spinal motor neurons, as well as neurons and neurites in brain, especially in the hippocampus and cortex of ubiquilin2-linked cases. The ubiquilin2-positive skein-like inclusions in spinal motor neurons also contained ubiquitin, p62, TDP43, FUS and optineurin, but not SOD1. Moreover, the ubiquilin2-positive inclusions were observed in spinal motor neurons in sporadic ALS and familial ALS cases, except in those with SOD1 mutations. Functional studies demonstrated that expression of mutant ubiquilin2 resulted in significantly higher accumulation of $Ub^{G76V}$-GFP than WT-ubiquilin 2, indicating an impairment of ubiquitin-mediated proteasomal degradation. Experiments conducted during development of embodiments of the present invention linked mutations of ubiquilin2 and defects in protein degradation pathway to neuronal degeneration in ALS and ALS/dementia, indicating a common pathogenic pathway with targets for rational therapies for these disorders.

A five-generation family with ALS, including 19 affected individuals, was identified (SEE FIG. 1). Clinical information was available from 40 individuals. There were 26 females and 16 males. ALS patients met the diagnosis of probable or definite ALS as defined in the revised EL-Escorial criteria and patient with dementia met the criteria for FTD or FTLD proposed by Nearly et al. The dementia was progressive and eventually global in most patients. There were seven patients with both ALS and dementia. Dementia preceded motor symptoms in some patients, but no patient remained free of motor involvement. In some patients, the motor involvement was initially of the upper motor neuron variety before lower motor neuron signs were observed. Seven patients had dementia, two males and three females. There were five obligate carriers, all female. Age at onset of symptoms was significantly earlier in males, but there was no difference in duration of disease. Three autopsied cases were examined, including a patient with early onset ALS/dementia (SEE Table 1).

TABLE 1

Clinical Data

| Individual | Gender | Age at onset | Duration (months) | Phenotype |
|---|---|---|---|---|
| Family A: | | | | |
| I: 2 | F | 45 | ≈48 | ALS |
| II: 2 | F | 62 | 60 | ALS |
| II: 4 | F | 58 | 84 | ALS |
| II: 6 | F | 62 | ≈60 | ALS |
| II: 7 | M | 19 | 24 | ALS |
| III: 1 | M | 25 | 59 | ALS |
| III: 3 | M | 33 | ≈36 | ALS |
| III: 4 | F | | | OBLIGATE: died age 72, asymptomatic |
| III: 5 | F | 52 | ≈84 | ALS |
| III: 6 | F | 53 | 47 | ALS |
| III: 9 | M | 33 | 24 | ALS |
| III: 10 | M | 35 | ≈48 | ALS |
| IV: 1 | F | 37 | 40 | ALS/Dementia |
| IV: 2 | F | | | OBLIGATE: living age 71, asymptomatic |
| IV: 3 | M | 49 | 25 | ALS |
| IV: 4 | F | 47 | 33 | ALS |
| IV: 5 | F | 42 | 24 | ALS |
| IV: 7 | M | 29 | 26 | ALS |
| IV: 8 | M | 38 | ≈24 | ALS |
| V: 1 | F | 41 | 36 | ALS |
| V: 3 | M | 47 | Living @ 43 | ALS |
| Family B: | | | | |
| I: 1 | M | 29 | 24 | ALS |
| II: 2 | F | 44 | 55 | ALS/dementia |
| II: 3 | F | 25 | 48 | ALS |
| II: 4 | F | 40 | 46 | ALS |
| II: 6 | F | 43 | 12 | ALS/dementia |
| III: 1 | F | 41 | 25 | ALS/dementia |
| III: 4 | F | 37 | Living @ 51 | ALS/dementia |
| III: 5 | M | 29 | 19 | ALS |
| Family C: | | | | |
| I: 2 | F | 42 | ≈60 | ALS |
| II: 1 | F | | | OBLIGATE: living age 50, asymptomatic |
| II: 3 | F | 40 | 84 | ALS/Dementia |
| III: 1 | M | 16 | Living @ 180 | Dementia/UMN signs |
| III: 4 | M | 22 | ≈60 | ALS/Dementia |
| Family D: | | | | |
| II: 4 | F | 53 | 36 | ALS |
| II: 5 | F | 59 | 27 | ALS |
| Family E: | | | | |
| II: 2 | F | | | OBLIGATE: died age 94, asymptomatic |
| II: 3 | F | | | OBLIGATE: died age 78, asymptomatic |
| III: 1 | F | 71 | 58 | ALS |
| III: 2 | M | 70 | 11 | ALS |

Male: mean age of onset 33.9 years, mean duration 43.1 months
Female: mean age of onset 47.3 years, mean duration 48.5 months DNA samples were obtained from 30 family members, including nine affected individuals and two obligate carriers. The disease was transmitted in a dominant fashion with reduced penetrance in females. Mutations in the known ALS-linked genes were excluded. Genome-wide linkage study with ABI Prism Set of microsatellite marker did not yield evidence of linkage with any autosomal marker. Because there was no evidence of male-to-male transmission of the disease, the family was screened with markers from the X chromosome. Linkage was established with several X chromosome microsatellite markers with the highest two-point Lod score of 5.0 with marker DXS9736 at θ=0 (SEE Table 2).

TABLE 2

| LOCUS Θ= | 0.000 | 0.050 | 0.100 | 0.150 | 0.200 | 0.300 | 0.400 |
|---|---|---|---|---|---|---|---|
| DXS1055 | −3.053 | 1.598 | 1.848 | 1.833 | 1.697 | 1.218 | 0.549 |
| DXS573 | 3.664 | 3.348 | 3.020 | 2.677 | 2.319 | 1.549 | 0.694 |
| DXS8023 | 3.367 | 3.074 | 2.770 | 2.452 | 2.119 | 1.403 | 0.609 |
| DXS988 | 4.797 | 4.393 | 3.972 | 3.532 | 3.071 | 2.076 | 0.968 |
| DXS991 | 4.971 | 4.551 | 4.113 | 3.655 | 3.176 | 2.143 | 0.992 |
| DXS8029 | 4.927 | 4.510 | 4.074 | 3.619 | 3.142 | 2.113 | 0.966 |
| DXS9736 | 4.982 | 4.562 | 4.124 | 3.667 | 3.187 | 2.154 | 1.003 |
| DXS981 | 4.638 | 4.248 | 3.841 | 3.415 | 2.969 | 2.003 | 0.926 |
| DXS1275 | −1.317 | 2.949 | 2.867 | 2.642 | 2.347 | 1.616 | 0.744 |

Note.
Two-point linkage analysis was conducted using the MLINK component of the LINKAGE software package (Lathrop G M, Lalouel J M. 1984). The trait was modeled as X-linked dominant with age dependent penetrance and with disease gene frequency of 0.001.

Detailed mapping with dense microsatellite markers and Illumina's Sentrix HumanHap300 Genotyping BeadChip defined the disease-causing gene in a 21.3 Mb minimum candidate region (MCR) between markers rs6417786 and DXS1275, which is located in the pericentric region from Xp11.23 to Xq13.1.

Figure 2A:
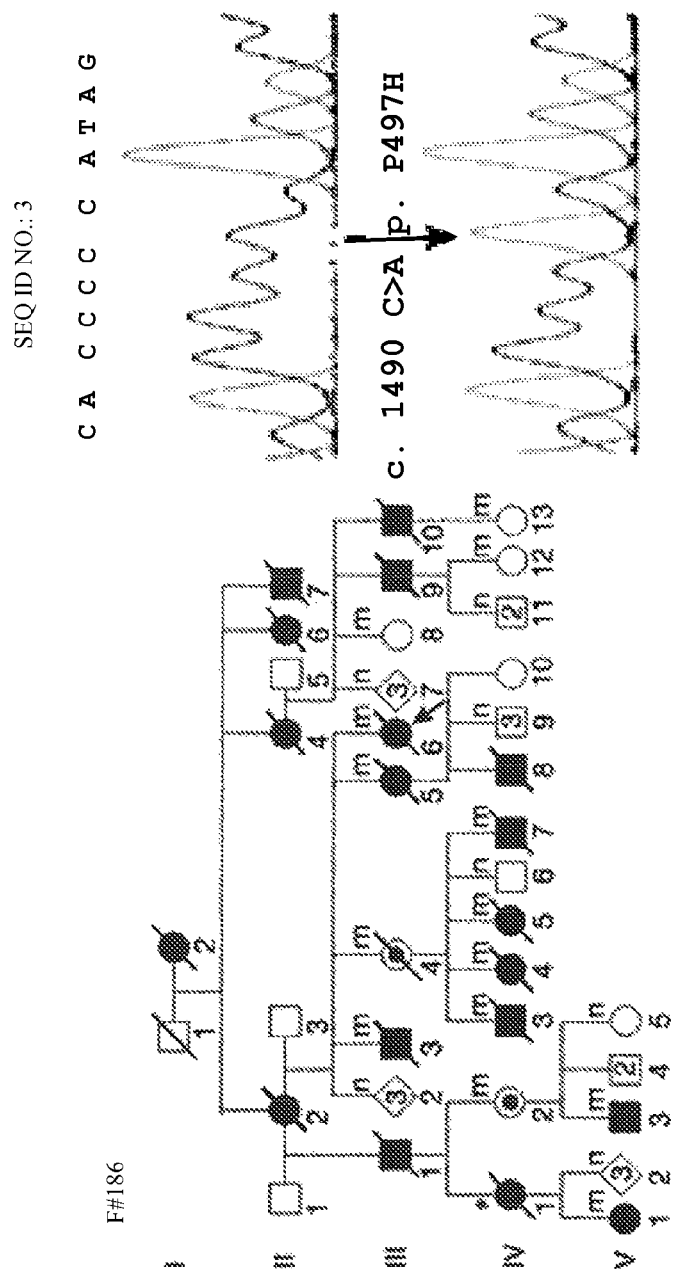
FIG. 2 shows mutations of the UBQLN2 in patients with ALS and ALS/dementia. (a) A mutation, c.1490C>A, resulting in P497H, was identified in a large family with ALS (F#186). This family was used for mapping of the X-chromosome-linked ALS. The pedigree is shown on the left and sequences are shown on the right. Wild type sequence is shown in the upper panel. A representative hemizygous mutation in a male patient (V3) is shown in the lower panel. All the affected members whose DNA samples were available for sequencing analysis had the mutation. Two obligate carriers (III4 and IV2) were identified to have the same mutation. For simplicity and clarity, more than one unaffected individual with both genders are represented by a single diamond and more than one unaffected male individual are represented by a single square. Individuals with mutation in the UBQLN2 are labeled by (m) and those without mutation are labeled by (n). (b) A mutation, c.1489C>T, resulting in P497S, was identified in F#9975. Shown in the right lower panel is a heterozygous mutation from a female patient (III1). (c) A mutation c.1516C>A, leading to P506T was identified in F#6313. Shown in the right lower panel is a heterozygous mutation from a female obligate carrier MO. (d) A c.1525 C>T, leading to P509S (III2), was identified in F#7700. Shown in the right lower panel is a hemizygous mutation in an asymptomatic case (III2) (e) A c.C1573T, resulting in P525S, was found in family F#6941. Shown in the right lower panel is a heterozygous mutation from the female patient (III1). (a-e) Probands are indicated with arrows and patients with dementia are indicated with asterisks. (f) Evolutionary conservation of amino acids in the mutated region of ubiquilin2 in different species. Comparison of human (*H. sapiens*) ubiquilin and its orthologues in chimpanzee (*P. troglodytes*), dog (*C. lupus familiaris*), cattle (*B. taurus*), mouse (*M. musculus*) and rat (*R. norvegicus*). Amino acids identical to human TRPV4 are in black letters and non-identical ones are denoted in red letters. The positions of the C-terminal amino acids are shown on the right. The mutated amino acids are indicated by arrows on the top.
Figure 2B:
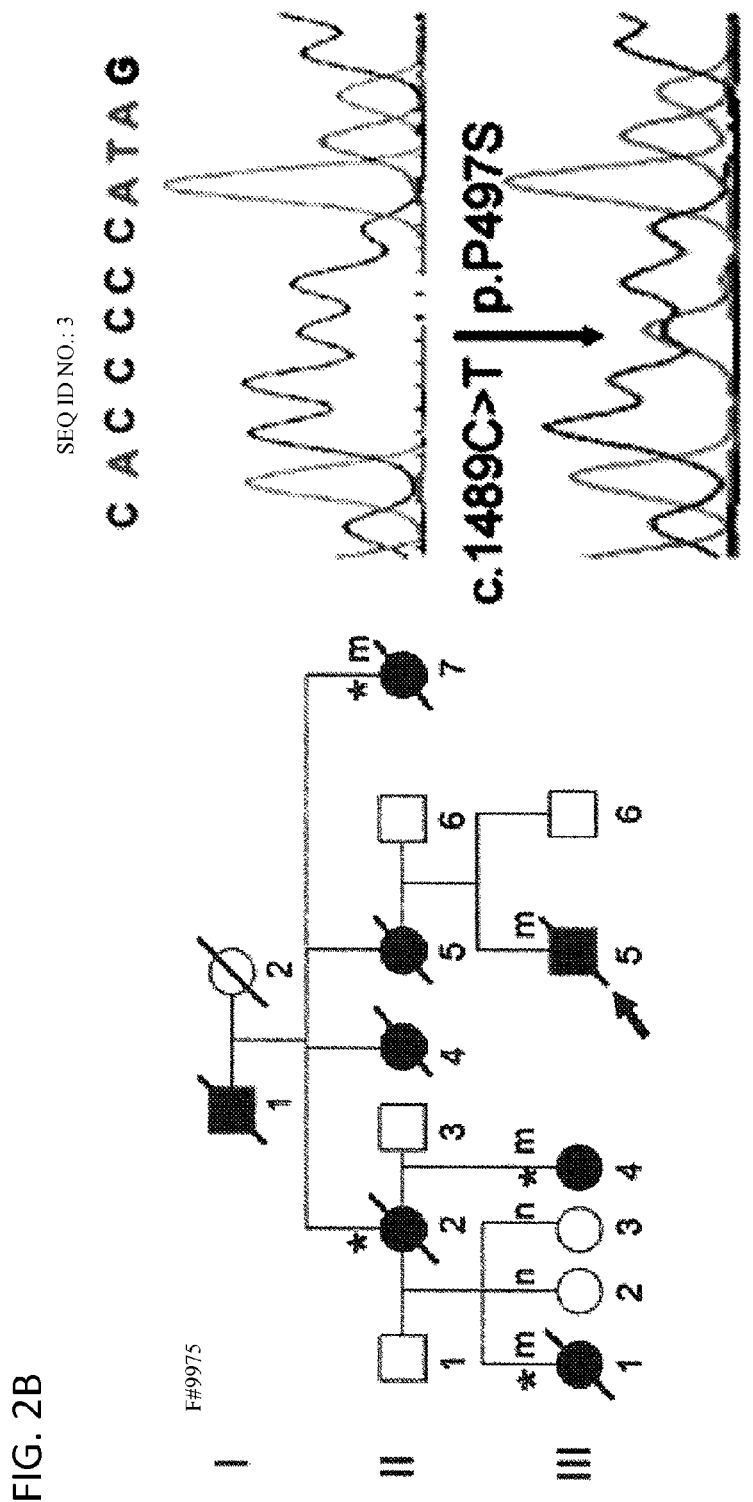
Figure 2C:
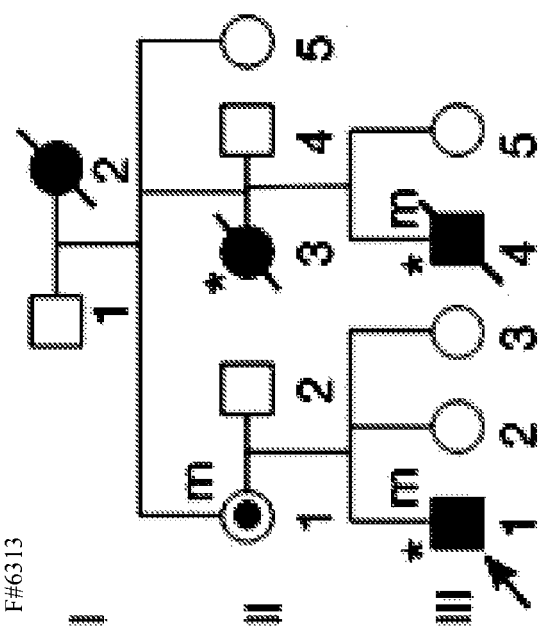
Figure 2D:
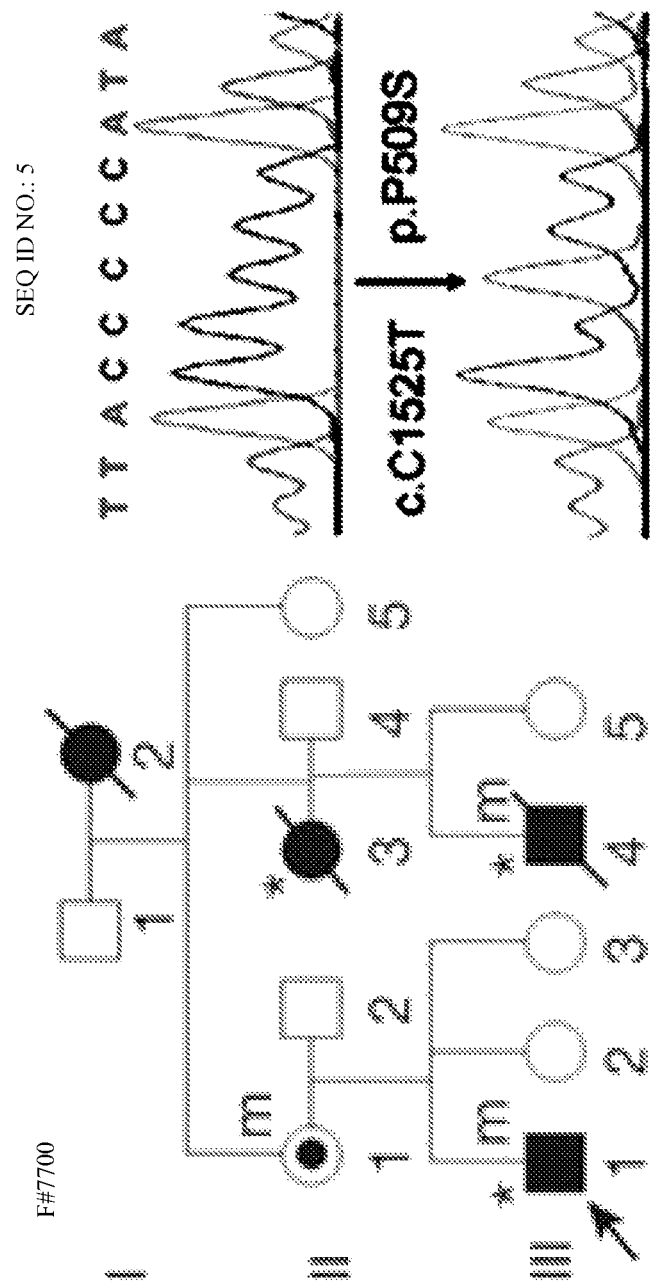
Figure 2E:
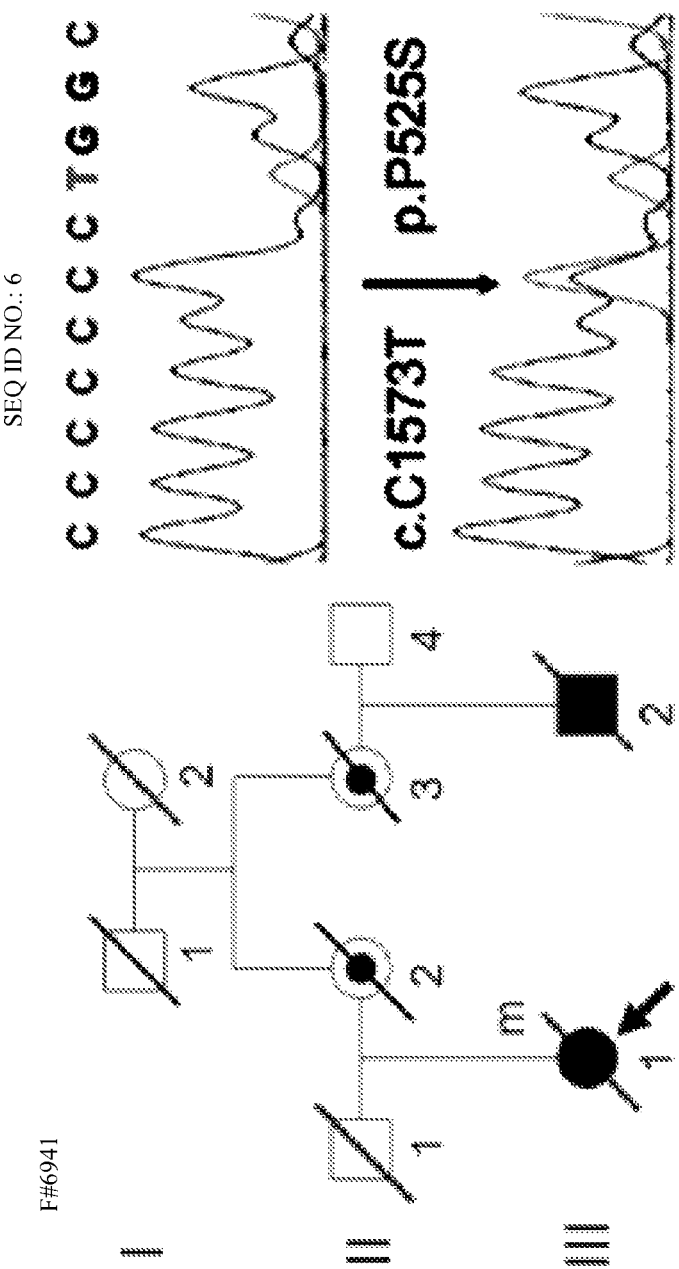

Genes in the MCR were analyzed based on the expression profile, function, structure and potential relevance to diseases of their encoded proteins. A total of 41 genes in the MCR were sequenced and a unique mutation was identified in the UBQLN2, which encodes ubiquilin 2 in this X-ALS family. This mutation, c.1490C>A, results in an amino acid substitution of proline by histine at codon 497 (P497H) (SEE FIG. 2a). The c.1490C>A mutation co-segregated with the disease in this large X-ALS pedigree (SEE FIG. 2a). This mutation was not present in the SNP database nor was it present in 928 control samples (1332 X chromosomes).

To test if mutations of the UBQLN2 are causative for ALS in other patients, 188 probands were analyzed from families with ALS or ALS/dementia, but without male-to-male transmission. Four other UBQLN2 mutations were identified in four unrelated families, including c.1489C>T (p.P497S), c.1516C>A (p.P506T), c.1525C>T (p.P509S) and c.1573C>T (p.P525S) (FIG. 1). All these mutations were hemizygous in the male patients and heterozygous in the female patients and obligate carriers. All the amino acids residues at the mutated site are conserved (SEE FIG. 2f). None of these mutations were present in SNP database and 928 control samples.

Figure 3:
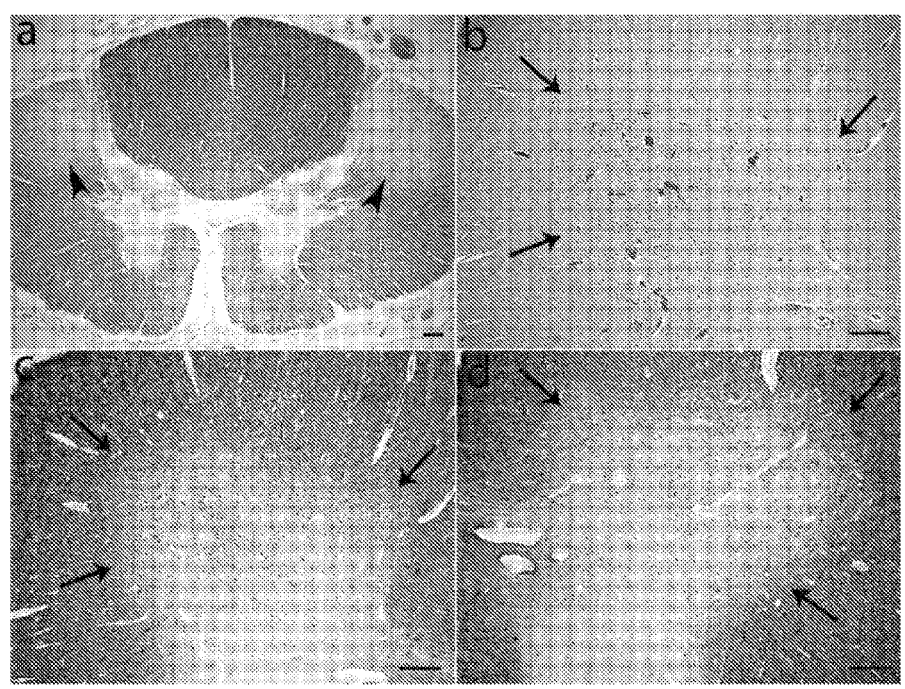
FIG. 3 shows pathology of spinal cord in X-linked ALS. Representative pathology of spinal cord from a patient with UBQLN2$^{P506T}$ mutation (F#6313, III4). (a) Myelin staining shows loss of myelin from the corticospinal tract (arrowheads). (b) Haematoxylin and eosin (H&E) staining shows loss of large neurons in the anterior horn (arrows). (c) Glial fibrillary acidic protein (GFAP) staining shows prominent astrocytosis in the anterior horns (arrows).

Clinic data was obtained from 35 patients with UBQLN2 mutations in these five families (See Table 2). Significant difference in age was observed at onset of disease between male and female patients, with male patients having earlier age of onset (33.9±14.0 vs. 47.3±10.8 years. However, the difference in duration of the disease was not statistically significant (43.1±42.1 vs. 48.5±19.9 months). Pathological analysis of spinal cord autopsy samples from three patients with P497H or P506T mutation revealed axonal loss in the corticospinal tract and loss of anterior horn cells and astrocytosis in the anterior hoen of the spinal cord (SEE FIG. 3).

Figure 4:
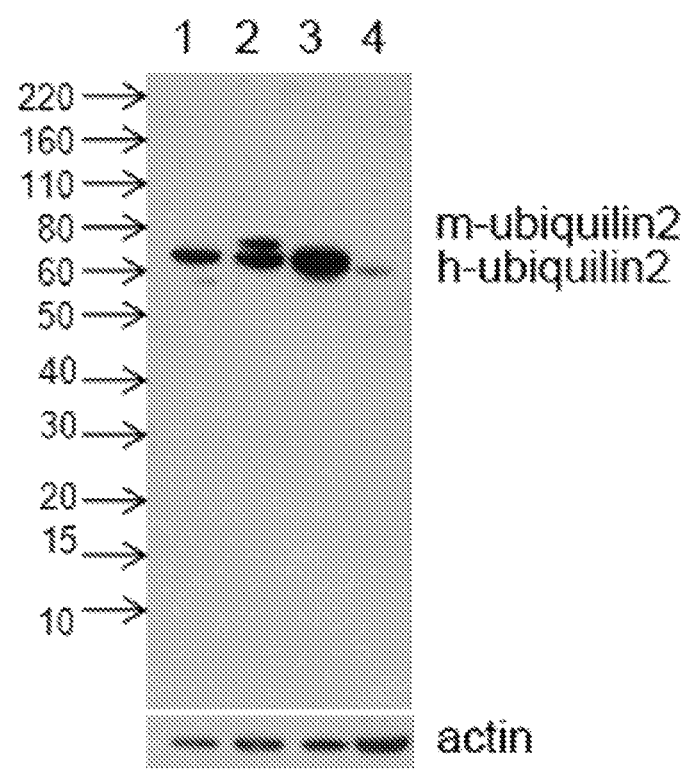
FIG. 4 shows Western blot with antibody to ubiquilin2. Antibody to the N-terminus of ubiquilin 2 (ubiquilin2-N) detects a single band of human or mouse ubiquilin2. Human UBQLN2-transfected SH-SY5Y (lane 1), neuro-2a (lane 2) and HEK293 cells (lane 3) and untransfected HEK293 cells. Mouse ubiquilin2 (m-ubiquilin2) and human ubiquilin2 (h-ubiquilin2) are indicated. Lower panel, actin control. Molecular weight is shown on the left in kilodaltons.
Figure 5:
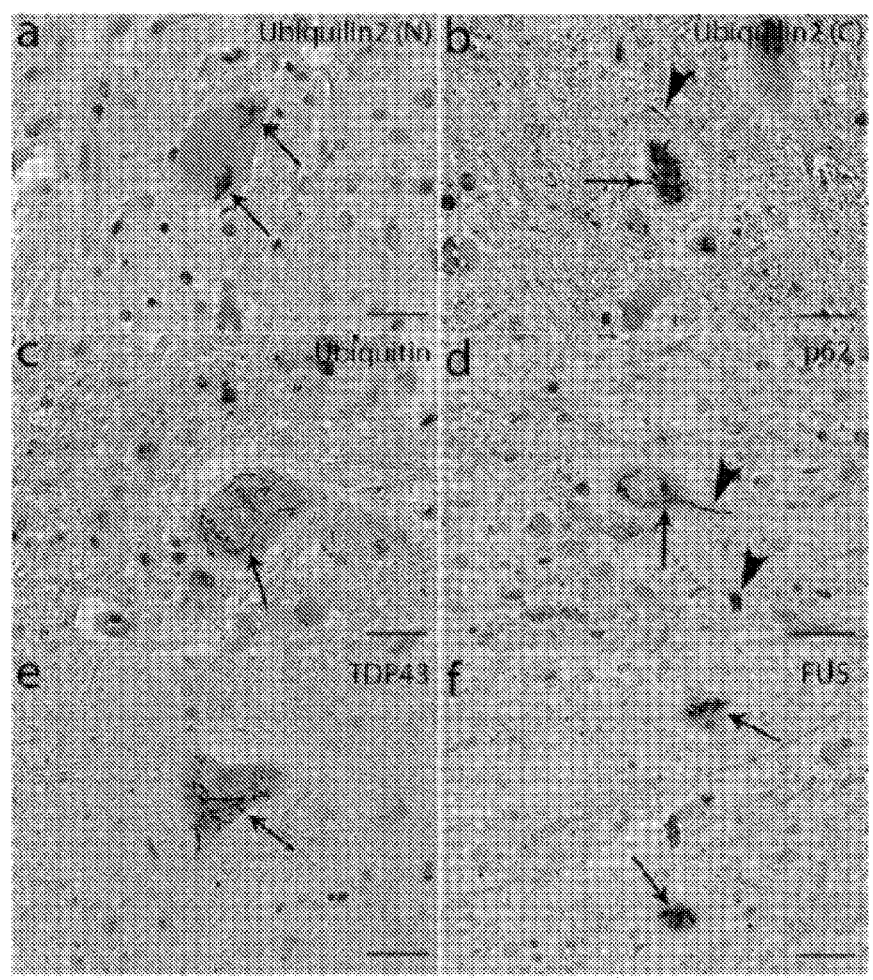
FIG. 5 shows representative immunoreactive skein-like inclusions in spinal motor neurons of a patient with P506T mutations in ubiquilin2. The skein-like inclusions are immunoreactive with antibodies against ubiquilin2 (a and b), ubiquitin (c), p62 (d), TDP43 (e) and FUS (f). (N), polyclonal antibody raised with a polypeptide at N-terminus; (c), monoclonal antibody raised with a polypeptide at C-terminus Scale bar, 100 μm.
Figure 6:
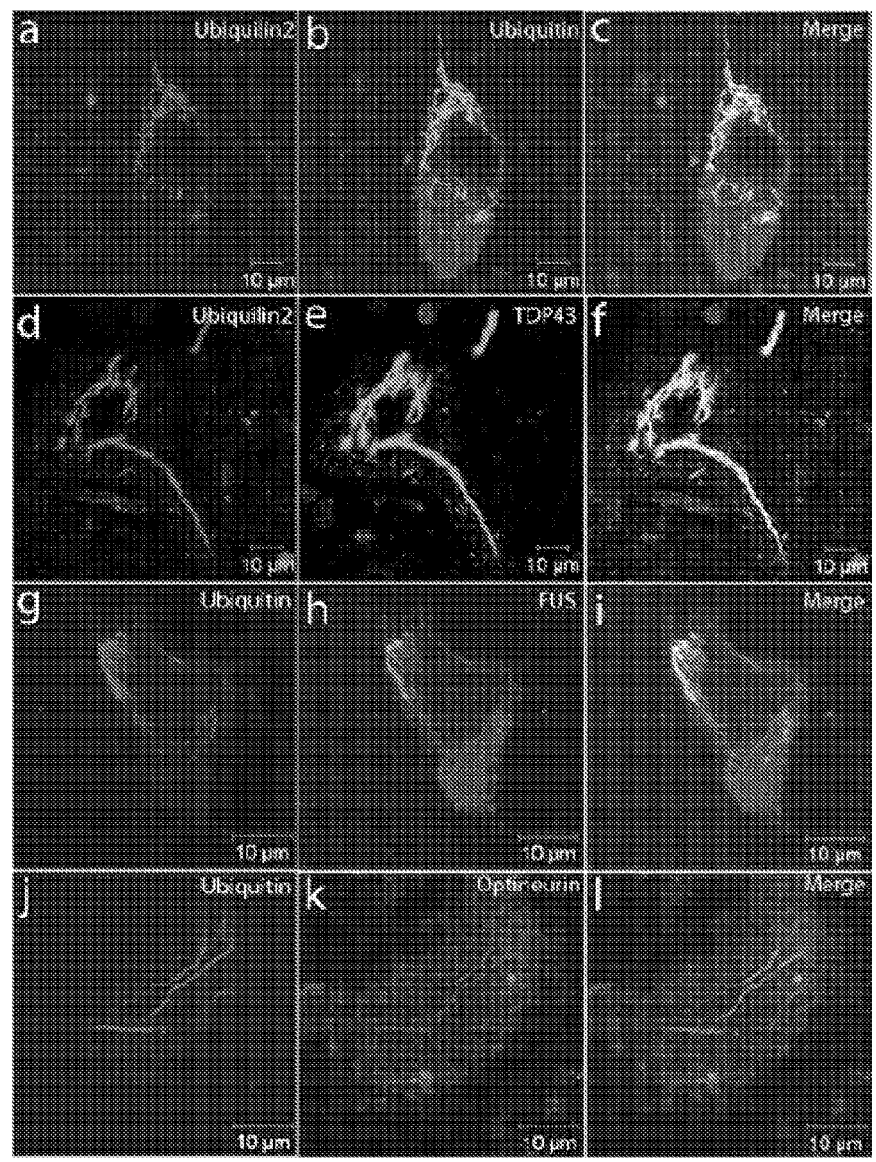
FIG. 6 shows co-localization of ubiquilin2 with other proteins involved in ALS. The skein-like inclusions in spinal cord sections from a patient with P506T mutation were studied using confocal microscopy. The ubiquil2 in-positive skein-like inclusions were immunoreactive with antibodies to ubiquitin (a-c), TDP43 (d-f), FUS (g-i) and optineurin (j-l).

Protein aggregates/inclusions have been recognized as a pathological hallmark in several neurodegenerative disorders, such as extracellular amyloid-beta plaques and intracellular tau neurofibrillary tangles in Alzheimer disease, and alpha-synuclein containing Lewy bodies in Parkinson disease (16). In ALS, protein aggregates/inclusions are most common in spinal motor neurons, and are typically skein-like in morphology. These ubiquitin positive inclusions are considered to be hallmark of ALS pathology (17, 18). Notably, several proteins that are mutated in small subsets of ALS, such as SOD1, TDP43, FUS and optineurin are prominent components of these inclusions (5, 7, 13, 19). To test if ubiquitin2 is present in the characteristic skein-like inclusions, immunohistochemical analysis of the autopsy spinal cord sections from patients with a P497H or P506T mutation was performed. Two different ubiquitin2 antibodies were used. One is a mouse monoclonal antibody raised with a polypeptide of 71 amino acids (aa) at the C-terminus (554aa-624aa, ubiquilin2-C) (H00029978-M03, Novus Biologicals Inc. Littleton, Colo.). The other is a rabbit polyclonal antibody generated by us using a polypeptide of 17aa at N-terminus (8aa-24aa, ubiquilin2-N). The polypeptide of 17aa is unique to ubiquilin2 and not present in other members of ubiquilin family or any known proteins. A single band of expected size was detected by Western blot using this new antibody (SEE FIG. 4). In immunohistochemistry, skein-like inclusions that were immunoreactive with both ubiquilin2-C and ubiquilin2-N antibodies were observed (SEE FIG. 5), suggesting that ubiquilin2 is involved in the inclusion formation in the X-ALS. The inclusions in the X-ALS case were also found to be immunoreactive with antibodies against other proteins that are known to be involved in the formation of the inclusions in other types of ALS. The skein-like inclusions in the X-ALS patient were also immunoreactive with antibodies against ubiquitin, p62, TDP43, FUS and optineurin, but not SOD1 (SEE FIGS. 5 and 6). Co-localization of ubiquilin2 with ubiquitin, TDP43, FUS and optineurin in the ubiquilin2-linked ALS case was verified with confocal microscopy (SEE FIG. 6).

Figure 7:
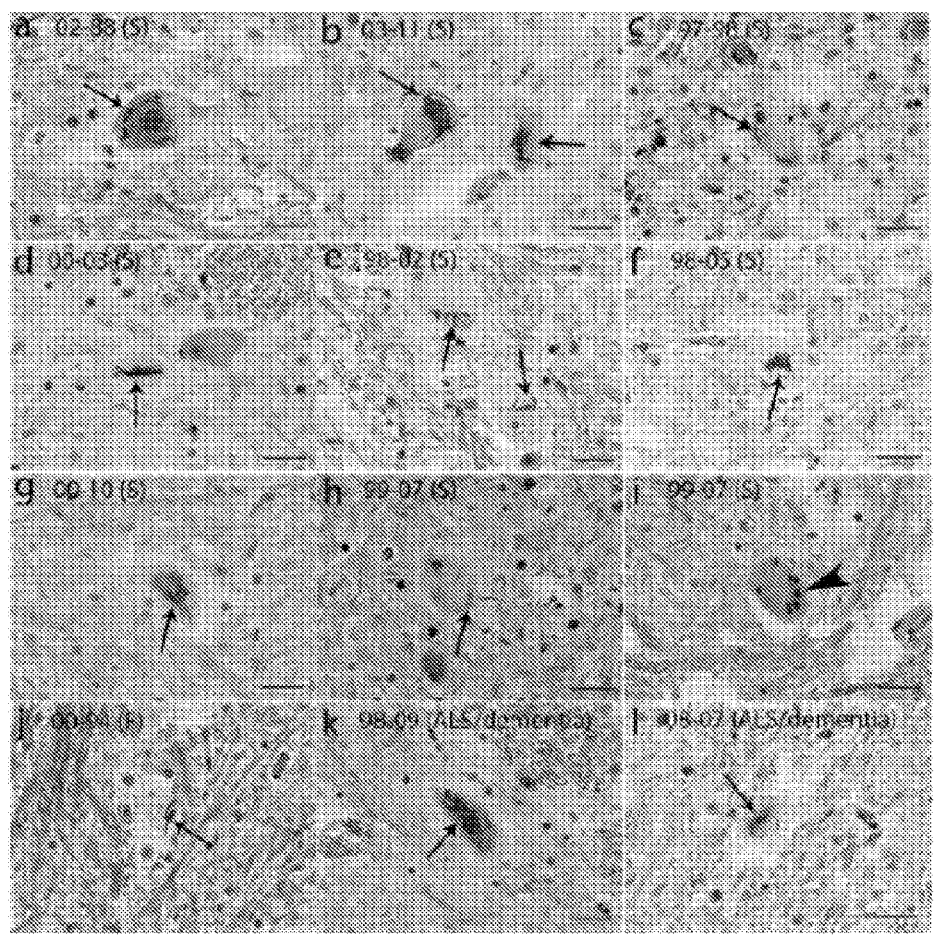
FIG. 7 shows ubiquilin2-immunoreactive inclusions in spinal cord sections from patients with SALS, FALS and ALS/dementia. Human spinal cord sections were analyzed with immunohistochemistry using a monoclonal antibody against ubiquilin2. Representative ubiquilin2-immunoreactive inclusions are shown here in anterior horn neurons in patients with SALS (a-i), FALS (j) and ALS/dementia (k and l). Most of the inclusions were skein-like (arrows), but some of them appeared to be compact (arrowhead). Both skein-like and compact inclusions could be observed in the same patients (h and i). The representative skein-like and ubiquilin2-positive inclusions are indicated by arrows. Autopsy numbers are labeled on the top of each panel. (S), SALS; (F), FALS. Scale bar, 100 μm.
Figure 8:
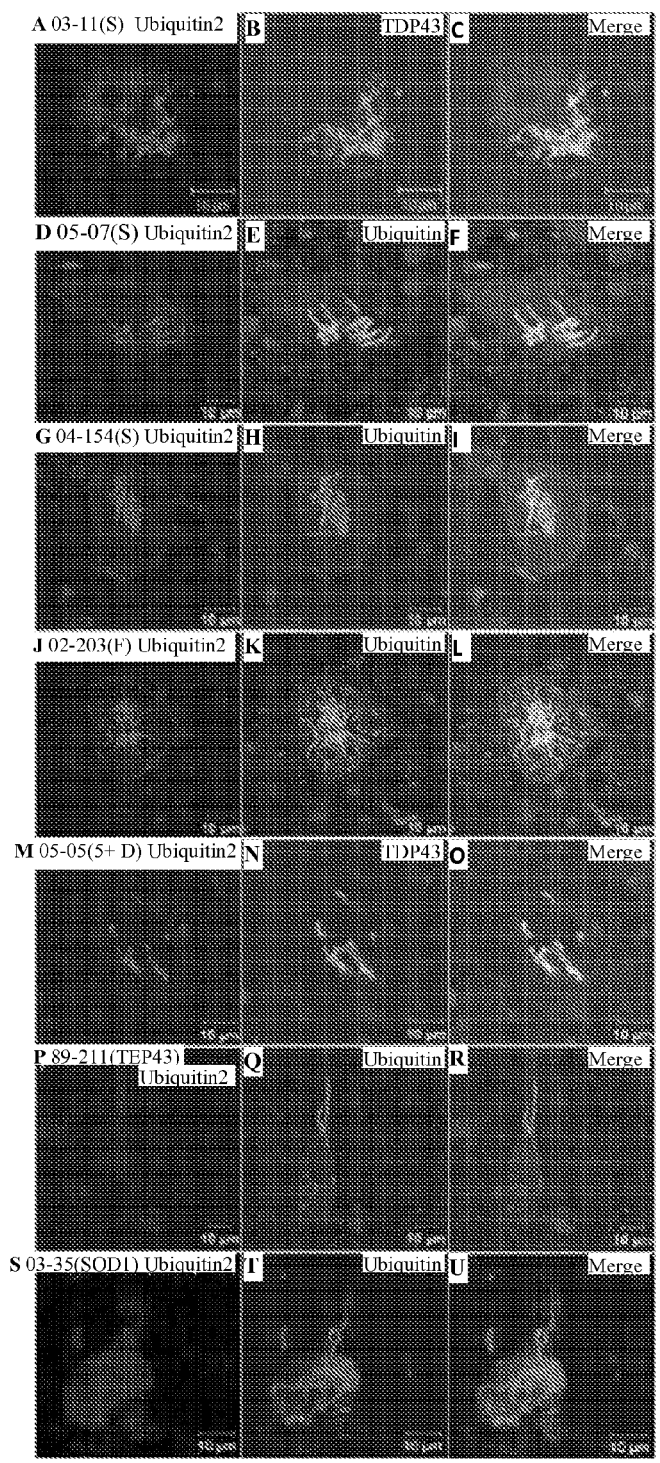
FIG. 8 shows co-localization of ubiquilin2-immunoreactive inclusions with other proteins involved in ALS in the spinal cord sections from cases with SALS, FALS and ALS/dementia. Shown here are representative ubiquilin2-immunoreactive inclusions co-localized with ubiquitin and TDP43, but not SOD1 in patients with SALS (a-i), FALS (j-l), sporadic ALS/dementia (m-o), TDP43-linked ALS (TDP43-G298S, p-r) and SOD1-linked ALS (SOD1-G85R, s-u). Autopsy numbers are labeled on the top of each panel. (S), SALS; (F), FALS; (S+D), SALS/dementia; TDP43 (TDP43-G298S); SOD1 (SOD1-G85R).

Mutations in TDP43, FUS or optineurin occur in a small fraction of ALS, but these proteins have been found to be major components in the inclusions of a wide spectrum of ALS (5, 7, 13, 19). To test if ubiquilin2 is involved in the inclusion formation of other types of ALS, autopsy spinal cord samples were examined, including: SALS, FALS without mutations in SOD1, TDP43 and FUS, ALS with dementia, FALS with SOD1 mutations (A4V, G85R, E100G), FALS with a G298S mutation in TDP43, and controls without ALS. The ubiquilin2-positive and skein-like inclusions were observed in all the ALS cases, except for controls and ALS cases with SOD1 mutations (SEE FIGS. 7 and 8), suggesting ubiquilin2 is a major component in the skein-like inclusions of other types of ALS, except for SOD1-linked ALS.

Figure 9:
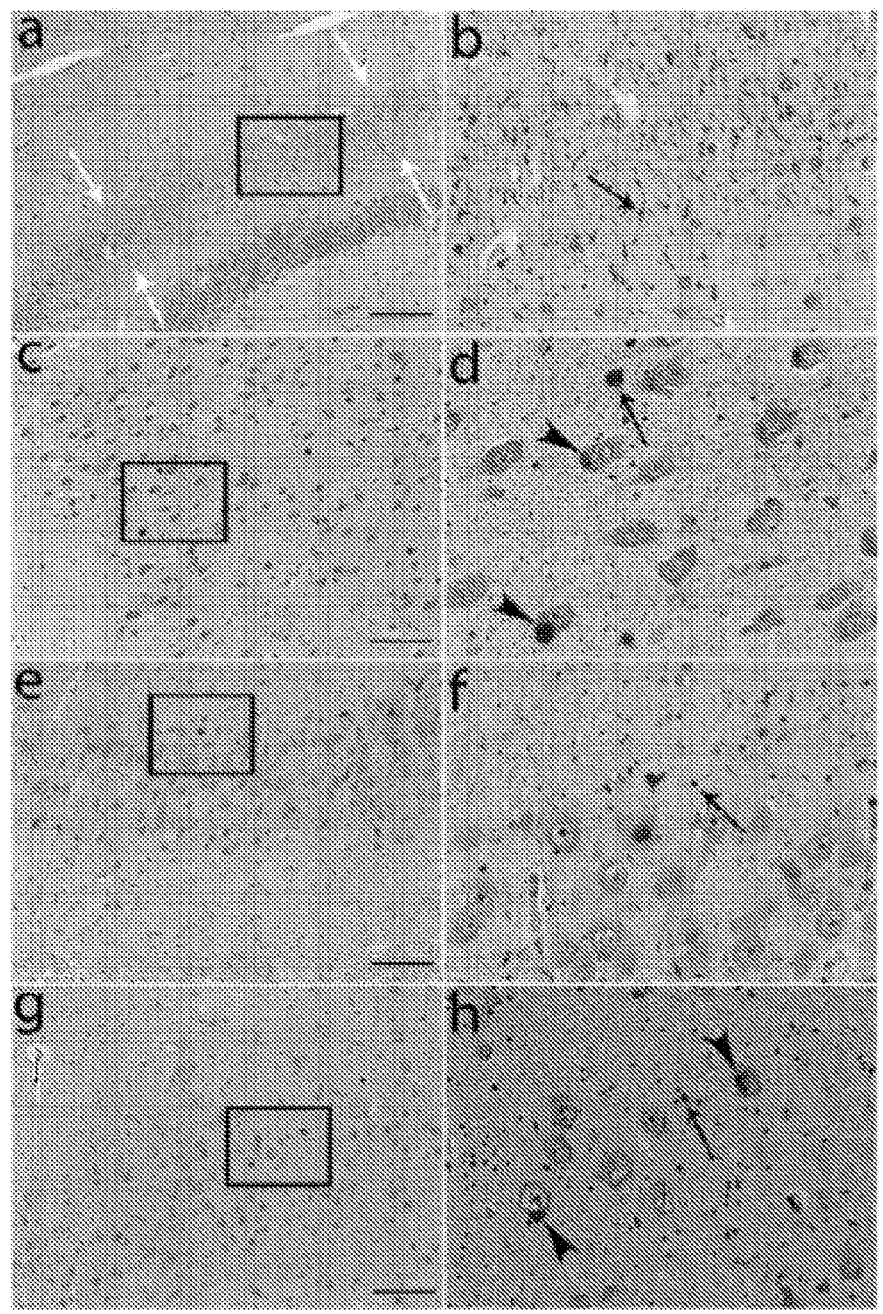
FIG. 9 shows Ubiquilin2-immunoreactive inclusions in the hippocampus. Brain sections from the hippocampus region of a patient with ubiquilin2-P506T mutation were analyzed using immunohistochemistry using a monoclonal antibody against ubiquilin2. The ubiquilin2-positive inclusions are shown in molecular layer (a and b), CA3 (c and d), CA2 (e and f) and CA1 (g and h). White arrows in panel (a) indicate the molecular layer with ubiquilin2 inclusions in the hippocampus. Black arrows indicate the representative inclusions in neurites and arrowheads indicate cytoplasmic inclusions in the cell bodies. Lower power images are shown on the left panels (a, c, e and g). Higher magnification images of the boxed areas on the left panels are shown on the right panels (b, d, f and h). Scale bar, 600 μm in panel (a) and 100 μm in panels (c, e and g).
Figure 10:
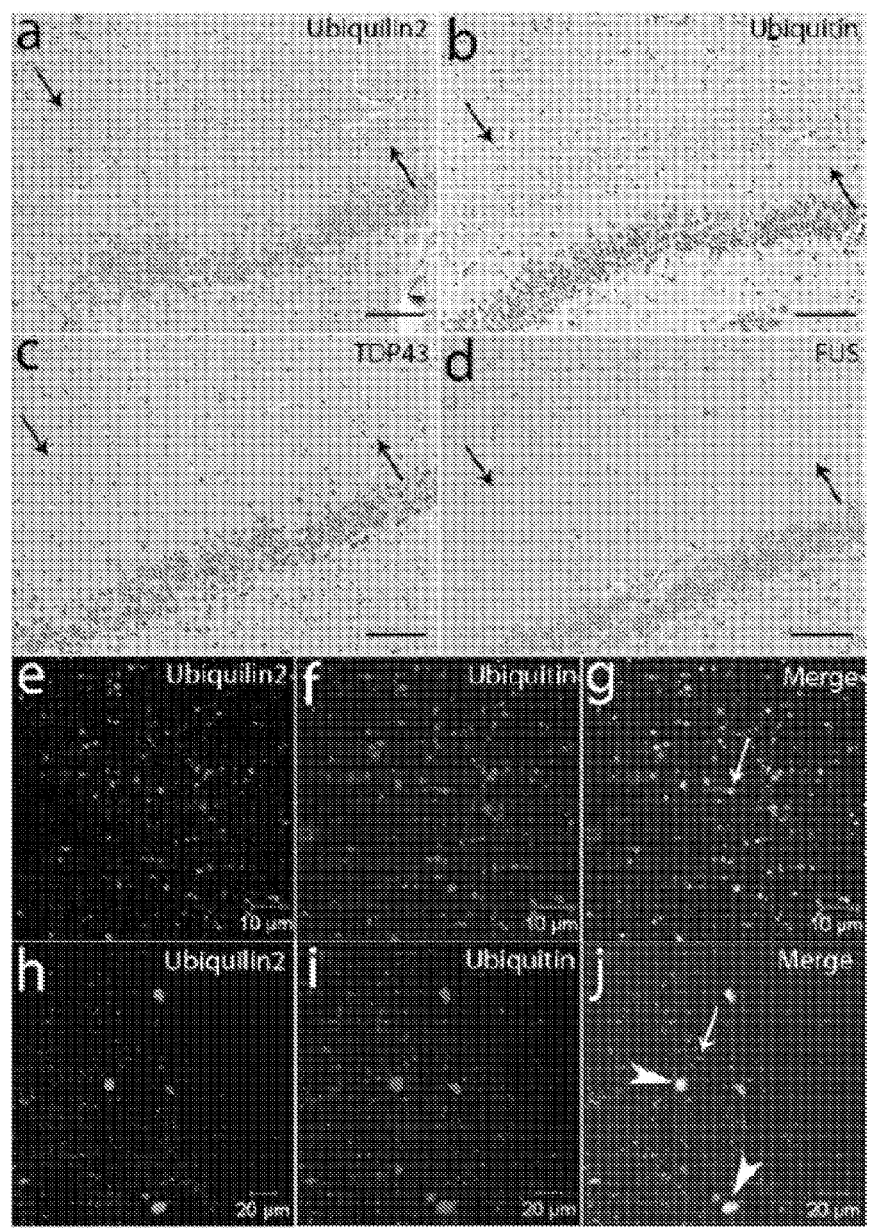
FIG. 10 shows co-localization of ubiquilin2 and ubiquitin in the inclusions in hippocampus. Brain sections from the hippocampus region of a patient with a ubiquilin2-P506T mutation were analyzed using immunohistochemistry (a-d) and confocal microscopy (e-j). Antibodies against ubiquilin2 N-terminus (a), ubiquitin (b), TDP43 (c) and FUS (d) were used for immunohistochemistry. Similar to the inclusions detected with ubiquilin2 monoclonal antibody, the immunoreactive inclusions were observed for ubiquilin2 polyclonal antibody (a) and ubiquitin in the molecular layer of hippocampus. But these inclusions appeared to be negative for TDP43 (c) and FUS (d). Arrows indicate the region of the molecular layer with or without substantial inclusions (a-d). Scale bar, 600 μm. For confocal microscopy (e-j), antibodies against ubiquilin2 (monoclonal, green) and ubiquitin (red) were used. Co-localization of ubiquilin2 and ubiquitin in the inclusions are shown in the regions of molecular layer (e-g) and CA1 (h-j) in the hippocampus. Representative neuritic and cytoplasmic inclusions are indicated by arrows and arrowheads, respectively.

Dementia is a prominent feature of some X-ALS cases. To examine if ubiquilin2-immunoreactive inclusions are present in brain and to explore the potential link between ubiquilin2 inclusions and dementia, brain autopsy samples from three X-ALS patients with either P497H or P506T were examined Widespread ubiquilin2 pathology was observed, and this pathology was most prominent in the hippocampus, though similar inclusions were se in the cortex (SEE FIGS. 9 and 10). Small ubiquilin2 inclusions were predominantly situated in the neuropil (1.5-5 µm in diameter). The fascia dentata presented a band of radially oriented dendritic and neuropil inclusions in the intermediate region of the molecular layer, while it lacked apparent immunostaining in granule cell bodies, supragranular and polymorphic regions. In addition to the small neuropil inclusions, large inclusions (up to 10-20 µm in diameter) were observed in some neurons, especially those in the CA1 and CA3 (SEE FIGS. 9 and 10). Myelinated axons in the white matter and bundled axons in the gray layers appeared to be free of these inclusions. These inclusions were also immunoreactive to ubiquitin antibodies, but seemed to be negative with antibodies to TDP43 and FUS (SEE FIG. 10). Co-localization of ubiquilin2 and ubiquitin in these inclusions were verified with Confocal microscopy (SEE FIG. 10).

Figure 11:
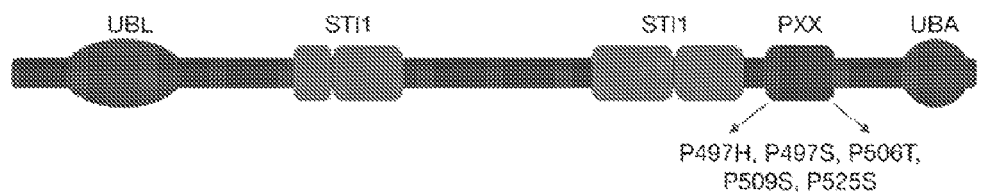
FIG. 11 shows predicted structural and functional domains of ubiquilin2. Ubiquilin2 is a protein of 624 amino acids. Predicted structural and functional domains include a UBL (ubiquitin-like domain, 33-103), four STI1 (heat shock chaperonin-binding motif), a 12 P-X-X repeats (491-526) and a UBA (ubiquitin-associated domain). ALS-linked mutations are clustered in the 12 P-X-X repeats.

Ubiquilin2 is a member of an ubiquitin-like protein family (ubiquilins) that share a high degree of similarity in eukaryotes ranging from yeast to mammals. Humans have four ubiquilin genes each encoding a separate protein. Ubiquilins are characterized by the presence of an N-terminal ubiquitin-like (UBL) domain and a C-terminal ubiquitin-associated (UBA) domain (SEE FIG. 11). The middle part of ubiquilins is highly variable. This structural organization is characteristic of proteins that function to deliver ubiquitinated proteins to the proteasome for degradation (20, 21). In accordance with this function, the UBL domain of ubiquilins binds subunits of the proteasome, and its UBA domain binds to polyubiquitin chains that are typically conjugated onto proteins marked for protein degradation in proteasome (21, 22). In addition to the UBL and UBA domains that are shared by all ubiquilins, ubiquilin2 has a unique repeat region containing 12 P-X-X tandem repeats (SEE FIG. 11). All the five ALS-linked mutations identified during development of embodiments of the present invention are located within this short P-X-X repeat region and exclusively involve proline residues (SEE FIG. 2F), indicating that these mutations may confer upon ubiquilin2 an unknown functional property that is related to the pathogenesis of ALS.

Figure 12:
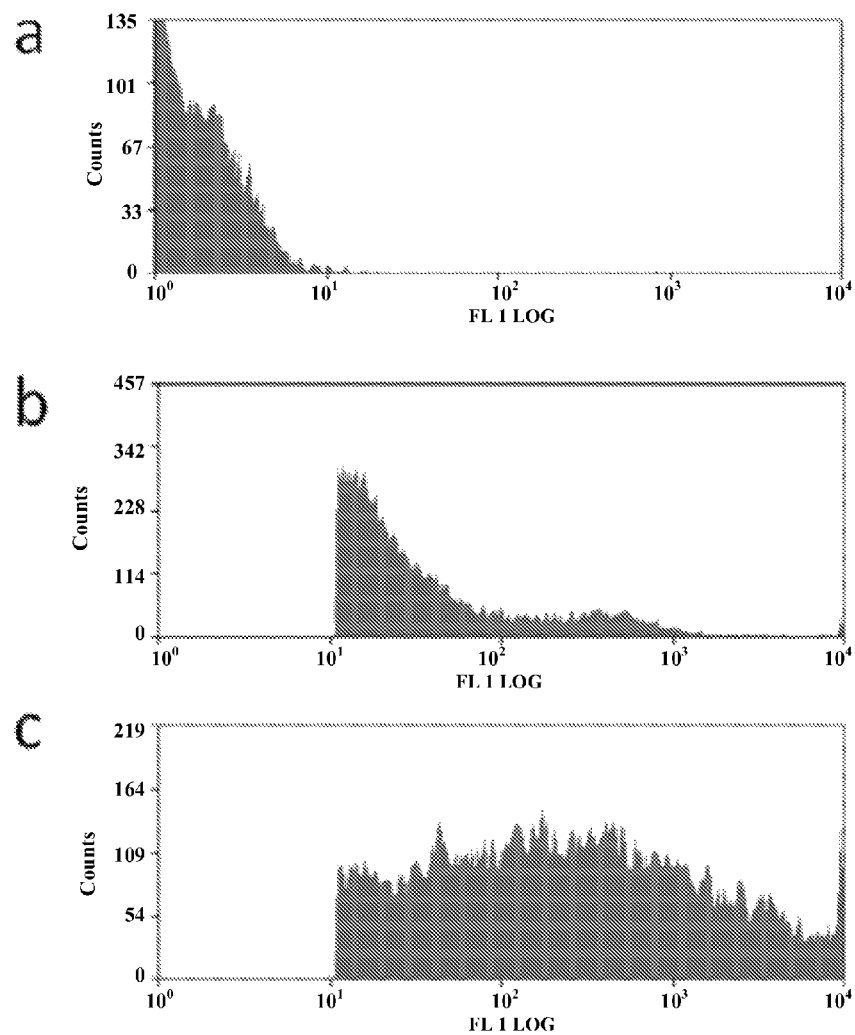
FIG. 12 shows flow-cytometric analysis of untransfected cells (a), $Ub^{G76V}$-GFP transfected cells (b), and $Ub^{G76V}$-GFP transfected cells treated for 24 hours with 5 µM of the proteasomal inhibitor, MG-132 (c). Incubation with MG-132 causes a marked increase in GFP fluorescence (FL1) intensity.
Figure 13:
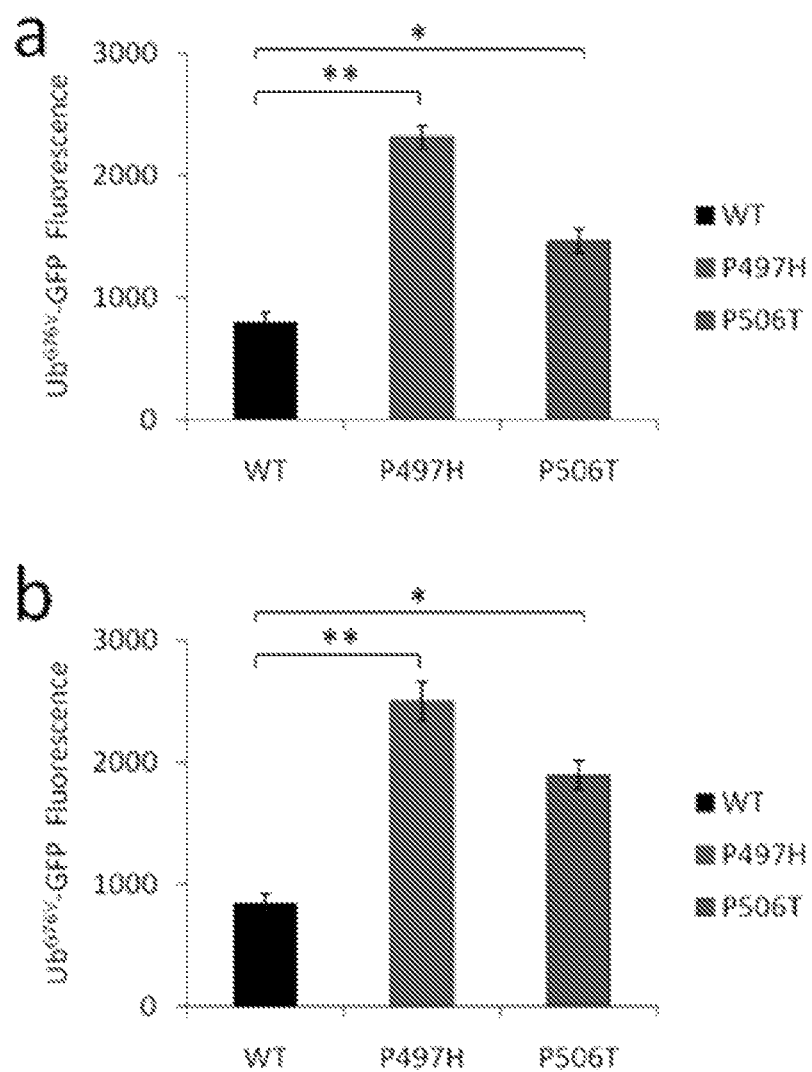
FIG. 13 shows mutations in ubiquilin2 lead to ubiquitin-mediated impairment of proteasomal degradation. $Ub^{G76V}$-GFP fluorescence intensity was quantified by FACS 48 hours post-transfection in (a) SH-SY5Y, and (b) Neuro2a cells transiently transfected with either wild-type (WT) or mutant ubiquilin2. Data are averaged from three independent experiments. Mean GFP fluorescence intensities are given. *$p<0.01$, **$p<0.001$ indicating significant differences when compared to wild-type (WT) ubiquilin2 (two-tailed Student's t test). Error bars, means±s.e.m.

Experiments were conducted during development of embodiments of the present invention to investigate the functional consequences of the mutant ubiquilin2 in protein degradation through the ubiquitin-proteasome system (UPS) was investigated. The UPS reporter substrate Ubiquitin$^{G76V}$-Green Fluorescent Protein (Ub$^{G76V}$-GFP) was used to test the effects of mutant ubiquilin2 on the ubiquitin-mediated protein degradation. Two mutations at two different sites were tested (P497H and P506T) using the Ub$^{G76V}$-GFP reporter system. The Ub$^{G76V}$-GFP reporter system carries an ubiquitin fusion degradation (UFD) signal, consisting of an N-terminal-linked ubiquitin molecule that serves as acceptor for polyubiquitin chains, through the canonical Lys48 and the less common Lys29 in the N-terminal-fused ubiquitin (20, 23). The G76V substitution prevents removal of the N-terminal-fused ubiquitin by cellular de-ubiquitinating enzymes, leading to efficient ubiquitination and proteasomal degradation of the Ub$^{G76V}$-GFP reporter (23). The functionality of the Ub$^{G76V}$-GFP reporter system was tested using proteasomal inhibitor MG-132 in transiently transfected cells. As expected, incubation with MG-132 resulted in remarkable accumulation of the Ub$^{G76V}$-GFP signal (SEE FIG. 12). The accumulation of Ub$^{G76V}$-GFP reporter in SH-SY5Y cells transiently transfected with either wild-type (WT) or mutant ubiquilin2 constructs was then examined. Expression of mutant ubiquilin2 resulted in significantly higher accumulation of Ub$^{G76V}$-GFP than WT-ubiquilin 2 (SEE FIG. 13a). Similar data were obtained using Neuro2a cell line that has some neuronal properties (SEE FIG. 13b), indicating an involvement of ubiquitin-mediated impairment in protein degradation.

Ubiquitin-positive skein-like inclusions are a characteristic hallmark in the spinal motor neurons in ALS cases. These inclusions may have different compositions of proteins depending on the causes. SOD1 has been observed in the inclusions in the SOD1-linked ALS and mutant SOD1 transgenic mouse models (24, 25), but not in the other forms of ALS. However, TDP43 and FUS have been observed in inclusions in TDP43- and FUS-linked ALS and other types of ALS, but not in SOD1-linked ALS (26-28). Experiments conducted during development of embodiments of the present invention demonstrated that neuronal and neuritic inclusions containing ubiquilin2 are a prominent pathology in spinal cord and hippocampus and cortex, two predominantly affected regions in patients with X-linked ALS and ALS/dementia, suggesting a pathogenic role of the ubiquilin2-containing inclusions in these disorders. Parallel to observations related to tau in Alzheimer disease, α-synuclein in Parkinson disease, and TDP43 and FUS in ALS, mutations in ubiquilin2 also account for only a small subset of ALS or ALS/dementia, but ubiquilin2 per se constitutes an obvious component in the inclusions that are associated with a wide spectrum of ALS, including SALS and ALS/dementia. This indicates a pathogenic role of the abnormal processing of ubiquilin2 in neuronal degeneration, not only in motor neurons, but also in other neurons as well.

Ubiquilin2 may act as a negative regulator of G protein-coupled receptor endocytosis and may also be involved in other neurodegenerative disorders (29, 30). Ubiquilins physically associate with the proteasome, ubiquitin ligases and a variety of other cellular proteins. Therefore, ubiquilins are thought to functionally link the ubiquitination machinery to the proteasome, and to affect protein degradation (21).

The removal of misfolded or damaged proteins is critical for optimal cell functioning. In the cytosol and nucleus, one of the two major proteolytic pathways to recycle misfolded or damaged proteins is the UPS (31). Though impaired UPS is associated with the formation of proteineous inclusions in the development of many neurodegenerative disorders, direct evidence of mutations in the UPS pathway is limited (32). Notably, mutations of parkin, a ubiquitin ligase, have been linked to autosomal recessive juvenile parkinsonism (33), and an 193M mutation of UCH-L1 was reported in a small German family with Parkinson disease (34), indicating involvement of UPS in PD. Experiments conducted during development of embodiments of the present invention demonstrated that mutations of ubiquilin2, a ubiquitin-like protein in five families with ALS and ALS/dementia, and that ubiquilin2-containing inclusions are a common pathological feature in a wide spectrum of ALS and ALS/dementia. Functional studies indicate an impairment of ubiquitin-mediated proteasomal degradation in cells expressing ALS-linked mutant ubiquilin2, thereby indicating impaired protein turnover in the pathogenic processes of ALS and ALS/dementia.

Experiments were conducted during development of embodiments of the present invention to identify mutation in the UBQLN4 gene and/or Ubiquilin4 protein that cause, are indicative of, are diagnostic of, and/or correlate to ALS in human subjects. 578 human cases of ALS were partially screened by single-strand conformation polymorphism (SSCP) analysis. Abnormal bands detected by SSCP were subjected to sequencing. 95 FALS patients were completely sequenced. 28 nucleotide polymorphisms were detected. Asp90Ala (D90A) from Patient 950685 in F9442 was not present among 332 controls. The nucleotide change from A to C (202A>C of NCBI Reference Sequence: NM_020131.3) removed an Alw I acting site. A new peptidase Asp N site was expected, but not approved. In silico experiments indicated that the mutation leads to alterations of physiochemical properties of Ubiquilin4, including changes in hydropathicity, average flexibility, polarity, and refractivity.

Accordingly, in some embodiments the present invention provides kits for the detection and characterization of ALS in a subject. In some embodiments, the kits contain reagents for detecting mutant Ubiquilin proteins (e.g., Ubiquilin2, Ubiquilin4, etc.) described herein and/or antibodies specific for ALS biomarkers, in addition to detection reagents and buffers. In other embodiments, the kits contain reagents specific for the detection of UBQLN (e.g., UBQLN2, UBQLN4, etc.) biomarker mRNA, mutations, cDNA (e.g., oligonucleotide probes or primers), etc. In preferred embodiments, the kits contain all of the components necessary to perform a detection assay, including all controls, directions for performing assays, and any necessary software for analysis and presentation of results. In some embodiments, kits comprise instructions (e.g. written, digital, and/or online) to perform assays for the detection and characterization of ALS.

In some embodiments, the expression of mRNA and/or proteins associated with UBQLN (e.g., UBQLN2, UBQLN4, etc.) mutations are provided. In some embodiments, the presence or absence of UBQLN mutations are correlated with mRNA and/or protein expression. In some embodiments, gene silencing (e.g., siRNA and/or RNAi) is utilized to alter expression of genes associated with mutations described herein.

In some embodiments, the present invention provides screening arrays of compounds (e.g., pharmaceuticals, drugs, peptides, or other test compounds) for their ability to alter expression, activity, structure, and/or interaction with other proteins, to compensate for altered function of the UBQLN genes and loci disclosed herein. In some embodiments, compounds (e.g., pharmaceuticals, drugs, peptides, or other test compounds) identified using screening assays of the present invention find use in the diagnosis or treatment of ALS.

In some embodiments, the present invention provides screening assays for assessing cellular behavior or function. For example, the response of cells, tissues, or organisms to interventions (e.g., drugs, diets, aging, etc.) may be monitored by assessing, for example, cellular functions using animal or cell culture models as describe herein. Such assays find particular use for characterizing, identifying, validating, selecting, optimizing, or monitoring the effects of agents (e.g., small molecule-, peptide-, antibody-, nucleic acid-based drugs, etc.) that find use in treating or preventing ALS or related diseases or conditions.

In some embodiments, the present invention provides methods for detection of expression of ALS markers (e.g., mutations in UBQLN2, UBQLN4, etc.). In some embodiments, expression is measured directly (e.g., at the RNA or protein level). In some embodiments, expression is detected in vivo or in vitro. In some embodiments, expression is detected in tissue samples (e.g., biopsy tissue). In other embodiments, expression is detected in bodily fluids (e.g., including but not limited to, plasma, serum, whole blood, mucus, and urine). In some embodiments, the present invention provides methods of identifying or characterizing ALS, or response thereof to therapy, based on the level expression of markers listed herein (e.g., mRNA or transcript levels).

The present invention further provides panels and kits for the detection of UBQLN (e.g., UBQLN2, UBQLN4, etc.) markers. In some embodiments, the presence of ALS marker is used to provide a diagnosis and/or prognosis to a subject. In some embodiments, the information provided is also used to direct the course of treatment. For example, if a subject is found to have a UBQLN (e.g., UBQLN2, UBQLN4, etc.) markers indicative of ALS, therapy or other interventions can be started at an earlier point when it is more likely to be effective. In some embodiments, assaying the presence or absence of UBQLN (e.g., UBQLN2, UBQLN4, etc.) ALS markers is performed after diagnosis of ALS, but prior to treatment. In some embodiments, assaying the presence or absence of UBQLN (e.g., UBQLN2, UBQLN4, etc.) ALS markers is performed after treatment of ALS.

Embodiments of present invention are not limited to the markers described herein. Any suitable marker that correlates with ALS or ALS onset or progression may be utilized. Additional markers are also contemplated to be within the scope of the present invention. Any suitable method may be utilized to identify and characterize ALS markers suitable for use in the methods of the present invention, including but not limited to, those described herein.

In some embodiments, UBQLN (e.g., UBQLN2, UBQLN4, etc.) ALS markers are detected by measuring the expression of corresponding mRNA in a tissue or other sample (e.g., a blood sample). mRNA expression may be measured by any suitable method, including but not limited to, those disclosed herein.

DNA or RNA markers may be detected, for example, by hybridization to an oligonucleotide probe. A variety of hybridization assays using a variety of technologies for hybridization and detection are available. For example, in some embodiments, TaqMan assay (PE Biosystems, Foster City, Calif.; See e.g., U.S. Pat. Nos. 5,962,233 and 5,538,848, each of which is herein incorporated by reference) is utilized. The assay is performed during a PCR reaction. The TaqMan assay exploits the 5'-3' exonuclease activity of the AMPLI-TAQ GOLD DNA polymerase. A probe composed of an oligonucleotide with a 5'-reporter dye (e.g., a fluorescent dye) and a 3'-quencher dye is included in the PCR reaction. During PCR, if the probe is bound to its target, the 5'-3' nucleolytic activity of the AMPLITAQ GOLD polymerase cleaves the probe between the reporter and the quencher dye. The separation of the reporter dye from the quencher dye results in an increase of fluorescence. The signal accumulates with each cycle of PCR and can be monitored with a fluorimeter.

In some embodiments, reverse-transcriptase PCR (RT-PCR) is used to detect the expression of RNA. In RT-PCR, RNA is enzymatically converted to complementary DNA or "cDNA" using a reverse transcriptase enzyme. The cDNA is then used as a template for a PCR reaction. PCR products can be detected by any suitable method, including but not limited to, gel electrophoresis and staining with a DNA specific stain or hybridization to a labeled probe. In some embodiments, the quantitative reverse transcriptase PCR with standardized mixtures of competitive templates method described in U.S. Pat. Nos. 5,639,606, 5,643,765, and 5,876,978 (each of which is herein incorporated by reference) is utilized.

In other embodiments, gene expression of ALS disease markers (e.g., mutants of UBQLN2, UBQLN4, etc.) is detected by measuring the expression of the corresponding protein or polypeptide. Protein expression may be detected by any suitable method. In some embodiments, proteins are detected by their binding to an antibody raised against the protein.

In some embodiments, the present invention provides therapies for ALS. In some embodiments, therapies target UBQLN markers of ALS (e.g., mutants of UBQLN2, UBQLN4, etc.).

EXPERIMENTAL

Example 1

Materials and Methods

Patients and Samples.

Experiments conducted during development of the present invention were approved by the local institutional review boards. ALS was diagnosed according to the El Escorial criteria (35) Some ALS cases had additional features of dementia and parkinsonism. The diagnosis of FTD was based on the revised criteria by Neary et al. (36). Pedigrees and clinical data were collected through specialists in neuromuscular diseases and were verified by medical records to establish diagnosis. DNA and other samples were taken after obtaining written informed consent. Overall, DNA from over 200 cases with ALS and 928 controls were used for genetic analysis. Autopsy samples, including brains and spinal cords from 48 cases were used for pathological and immunohistological studies.

Genetic Analysis.

Genomic DNA was extracted from whole peripheral blood, transformed lymphoblastoid cell lines or available tissues by standard methods (Qiagen, Valencia, Calif.). Intronic primers flanking exons were designed at least 50 nucleotides away from the intron/exon boundary. When a PCR product was over 500 bp, multiple overlapping primers were designed with an average of 50 bp overlap. Forty nanograms of genomic DNA were used for PCR amplification. The amplification protocol consisted of the following steps: incubation at 95° C. for 1 min, 32 cycles of 95° C. (30 s), 55° C. (30 s) and 72° C. (1 min) and a final 5 min extension at 72° C., with modifications when necessary. The PCR-amplified DNA product were separated by 1.5% agarose gel and the specific PCR product was cut out from the gel and purified using QIAquick Gel Extraction Kit (QIAGEN Science, Maryland). For sequencing of a PCR product, fluorescent dye labeled single strand DNA was amplified with Beckman Coulter sequencing reagents (GenomeLab DTCS Quick Start Kit) followed by single pass bi-directional sequencing with CEQ™ 8000 Genetic Analysis System (Beckman Coulter, Fullerton, Calif.).

Antibodies, Immunohistochemistry and Confocal Microscopy.

Two anti-ubiquilin2 antibodies were used. One was raised in rabbit using a polypeptide of human ubiquilin2 (8aa-24 aa, NH2-SGPPRPSRGPAAAQGSA-COOH). The anti-serum was affinity-purified. The other ubiquilin2 antibody was mouse monoclonal (5F5, Cat# H00029978-M03), which was purchased from Novus Biologicals Inc. Littleton, Colo.). Other antibodies against ubiquitin, p62, TDP43, FUS and SOD1, and the basic protocols for immunohistochemistry and confocal microscopy were described in detail in previous study (26). 6 m sections were cut from formalin-fixed, paraffin-embedded spinal cord and brain regions containing frontal lobe or hippocampus. The sections were deparaffinized and rehydrated with xylene, a series of diluted ethanol and water. The antigens in the sections were retrieved using a high pressure decloaking chamber (26). For immunohistochemistry, the endogenous peroxidase activities were blocked with 2% hydrogen peroxide. Nonspecific background was blocked with 1% bovine serum albumin. Eight different antibodies against ubiquilin2 or other proteins were used as primary antibodies. These antibodies included ubiquilin2-N (0.5 g/ml, generated by ourselves), mouse anti-ubiquilin2 monoclonal antibody (H00029978-M03, 0.2 g/ml, Novus Biologicals, Littleton, Colo.), rabbit anti-FUS polyclonal antibody (11570-1-AP, 3 g/ml, Proteintech Group, Chicago, Ill.), mouse anti-TDP43 monoclonal antibody (60019-2-Ig, 1 g/ml, Protein Tech Group, Chicago, Ill.), rabbit anti-TDP43 polyclonal antibody (10782-2-AP, 0.1 g/ml, Protein Tech Group), mouse anti-ubiquitin monoclonal antibody (10R-U101B, 0.5 g/ml, Fitzgerald Industries International, Concord, Mass.), goat anti-ubiquitin polyclonal antibody (sc-6085, Santa Cruz Biotechnology, Santa Cruz, Calif.), mouse anti-p62 monoclonal antibody (H00008878-M01, 1 g/ml, Abnova Coporation, Taipei, Taiwan) and two rabbit anti-optineurin polyclonal antibodies (C-term, 100000, 0.2 g/ml, or INT, 100002, 3 g/ml, Cayman Chemical, Ann Arbor, Mich.). Biotinylated goat anti-rabbit or anti-mouse IgG was used as the secondary antibody Immunoreactive signals were detected with peroxidase-conjugated streptavidin (Bio-Genex, San Ramon, Calif.) using 3-amino-9-ethylcarbazole as a chromogen.

For confocal microscopy, antibodies generated in different species were used with different combinations. These antibodies included those against ubiquilin2, FUS, TDP43, p62, optineurin and ubiquitin. Fluorescence signals were detected with donkey anti-rabbit IgG conjugated with fluorescein isothiocyanate (Thermo Scientific, Rockford, Ill.) and goat anti-mouse IgG conjugated with rhodamine (R-6393, Invitrogen, Carlsbad, Calif.) using an LSM 510 META Laser Scanning Confocal Microscope with the multitracking setting. The same pinhole diameter was used to acquire each channel.

Western Blot.

Western blot was performed using the protocol previously described (26). Briefly, spinal cord tissues from the lumbar segments were processed and homogenized. Supernatants were subject to total protein quantification, gel electrophoresis and blotted on PVDF membranes. Ubiquilin2 was detected using antibody ubiquilin2-N (0.5 g/ml, generated by us) using an ECL kit (GE Bio-sciences, Piscataway, N.J.). The membranes were striped and blotted with an antibody against actin.

Expression Constructs.

A full length human cDNA clone (*Homo sapiens* ubiquilin 2, IMAGE: 4543266) was used as a template for construction of the expression constructs. Two primers anchored with an XhoI (ubiquilin2-TP1,5'-ttctcgagggccgccatggctgagaat-3' (SEQ ID NO.: 1)) and BamHI (ubiquilin2-TP2,5'-catggatc-ctgtatgtctgtattacc-3'(SEQ ID NO.: 2)) were used to amplify the full length coding sequence. The amplified fragment was cloned into plasmid vector pBluescript M13. The ubiquilin2 sequence was verified by direct sequencing. Each of the P497H and P506T mutations was introduced into the plasmid vector by site-directed mutagenesis using a primer containing respective mutation. The XhoI/BamHI fragment containing wild-type UBQLN2, UBQLN2P497H or UBQLN2P506T was released from the pBluescript M13 vector and cloned into the XhoI and BamHI sites of a dual expression vector pIRES2-ZsGreen1 or pIRES2-DsRed2 (Clontech, Mountain View, Calif.).

Expression of Wild-Type and Mutant Ubiquilin2.

Human embryonic kidney cells (HEK293) and Neuro2a cells were grown on collagen-coated glass coverslips in Dulbecco's modified Eagle's medium containing 10% (v/v) human serum, 2 mM L-glutamine, 2 U/ml penicillin, and 2 mg/ml streptomycin at 37° C. in a humidity-controlled incubator with 5% CO2. The cells were transiently transfected with expression vectors wild-type UBQLN2, UBQLN2P497H or UBQLN2P506T using Lipofectamine 2000 (Invitrogen).

UPS Reporter Assay.

SH-SY5Y and Neuro2a cells were grown in 24-well plates and double-transfected with the UPS reporter (20) vector containing UbG76V-GFP (Addgene plasmid #11941) and a dual expression vector containing DsRed2 with either wild-type or mutant Ubiquilin 2. Forty-eight hours post-transfection, cells were harvested and resuspended in PBS. UbG76V-GFP transfected cells were used for control experiments to test the functionality of the UPS reporter. In these experiments, media was changed 24-hours post-transfection to that containing 5 μM of the proteasomal inhibitor MG-132 (A.G. Scientific, Inc, San Diego, Calif.). Cells were incubated in this media for 24 hours and then harvested and resuspended in PBS. All flow cytometric data were collected and analyzed using a MoFlo cell sorter and Summit software (DakoCytomation, Fort Collins, Colo.). The argon-ion (488 nm) and yellow (565 nm) lasers were used for excitation. The GFP and DsRed2 signals were collected using 530/40 nm and 600/30 nm bandpass filters, respectively. In all experiments data were gated on GFP/DsRed2 dual labeled cells. At least 500 such events were recorded. The DsRed2 expression levels and profiles were similar across experiments. Data were collected from three independent experiments. Two tailed unpaired Student's t-test (p<0.05) was used for statistical analysis.

Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the claims.

REFERENCES

All references provided herein and/or listed below are incorporated by reference in their entireties.
1. Deng H X, Hentati A, Tainer J A, Iqbal Z, Cayabyab A, Hung W Y, et al. Amyotrophic lateral sclerosis and structural defects in Cu,Zn superoxide dismutase. Science. 1993; 261(5124):1047-51.
2. Rosen D R, Siddique T, Patterson D, Figlewicz D A, Sapp P, Hentati A, et al. Mutations in Cu/Zn superoxide dismutase gene are associated with familial amyotrophic lateral sclerosis. Nature. 1993; 362(6415):59-62.
3. Kabashi E, Valdmanis P N, Dion P, Spiegelman D, McConkey B J, Vande Velde C, et al. TARDBP mutations in individuals with sporadic and familial amyotrophic lateral sclerosis. Nat. Genet. 2008; 40(5):572-4.
4. Sreedharan J, Blair I P, Tripathi V B, Hu X, Vance C, Rogelj B, et al. TDP-43 mutations in familial and sporadic amyotrophic lateral sclerosis. Science. 2008; 319(5870):1668-72.
5. Van Deerlin V M, Leverenz J B, Bekris L M, Bird T D, Yuan W, Elman L B, et al. TARDBP mutations in amyotrophic lateral sclerosis with TDP-43 neuropathology: a genetic and histopathological analysis. Lancet Neurol. 2008; 7(5):409-16.
6. Kwiatkowski T J, Jr., Bosco D A, Leclerc A L, Tamrazian E, Vanderburg C R, Russ C, et al. Mutations in the FUS/TLS gene on chromosome 16 cause familial amyotrophic lateral sclerosis. Science. 2009; 323(5918):1205-8.
7. Vance C, Rogelj B, Hortobagyi T, De Vos K J, Nishimura A L, Sreedharan J, et al. Mutations in FUS, an RNA processing protein, cause familial amyotrophic lateral sclerosis type 6. Science. 2009; 323(5918):1208-11.
8. Chen Y Z, Bennett C L, Huynh H M, Blair I P, Puls I, Irobi J, et al. DNA/RNA helicase gene mutations in a form of juvenile amyotrophic lateral sclerosis (ALS4). Am J Hum Genet. 2004; 74(6):1128-35.
9. Greenway M J, Andersen P M, Russ C, Ennis S, Cashman S, Donaghy C, et al. ANG mutations segregate with familial and 'sporadic' amyotrophic lateral sclerosis. Nat. Genet. 2006; 38(4):411-3.
10. Nishimura A L, Mitne-Neto M, Silva H C, Richieri-Costa A, Middleton S, Cascio D, et al. A mutation in the vesicle-trafficking protein VAPB causes late-onset spinal muscular atrophy and amyotrophic lateral sclerosis. Am J Hum Genet. 2004; 75(5):822-31.
11. Yang Y, Hentati A, Deng H X, Dabbagh O, Sasaki T, Hirano M, et al. The gene encoding alsin, a protein with three guanine-nucleotide exchange factor domains, is mutated in a form of recessive amyotrophic lateral sclerosis. Nat. Genet. 2001; 29(2):160-5.
12. Chow C Y, Landers J E, Bergren S K, Sapp P C, Grant A E, Jones J M, et al.
Deleterious variants of FIG4, a phosphoinositide phosphatase, in patients with ALS. Am J Hum Genet. 2009; 84(1):85-8. PMCID: 2668033.
13. Maruyama H, Morino H, Ito H, Izumi Y, Kato H, Watanabe Y, et al. Mutations of optineurin in amyotrophic lateral sclerosis. Nature. 2010; 465(7295):223-6.
14. Ticozzi N, LeClerc A L, Keagle P J, Glass J D, Wills A M, van Blitterswijk M, et al. Paraoxonase gene mutations in amyotrophic lateral sclerosis. Ann Neurol. 2010; 68(1):102-7.
15. Mitchell J, Paul P, Chen H J, Morris A, Payling M, Falchi M, et al. Familial amyotrophic lateral sclerosis is associated with a mutation in D-amino acid oxidase. Proc Natl Acad Sci USA. 2010; 107(16):7556-61. PMCID: 2867752.
16. Lansbury P T, Lashuel H A. A century-old debate on protein aggregation and neurodegeneration enters the clinic. Nature. 2006; 443(7113):774-9.
17. Leigh P N, Whitwell H, Garofalo O, Buller J, Swash M, Martin J E, et al. Ubiquitin-immunoreactive intraneuronal inclusions in amyotrophic lateral sclerosis. Morphology, distribution, and specificity. Brain. 1991; 114 (Pt 2):775-88.
18. Lowe J. New pathological findings in amyotrophic lateral sclerosis. J Neurol Sci. 1994; 124 Suppl:38-51.
19. Shibata N, Hirano A, Kobayashi M, Dal Canto M C, Gurney M E, Komori T, et al. Presence of Cu/Zn superoxide dismutase (SOD) immunoreactivity in neuronal hyaline inclusions in spinal cords from mice carrying a transgene for Gly93Ala mutant human Cu/Zn SOD. Acta Neuropathol (Berl). 1998; 95(2):136-42.
20. Dantuma N P, Lindsten K, Glas R, Jenne M, Masucci M G. Short-lived green fluorescent proteins for quantifying ubiquitin/proteasome-dependent proteolysis in living cells. Nat. Biotechnol. 2000; 18(5):538-43.
21. Su V, Lau A F. Ubiquitin-like and ubiquitin-associated domain proteins: significance in proteasomal degradation. Cell Mol Life Sci. 2009; 66(17):2819-33. PMCID: 2725189.
22. Rothenberg C, Monteiro M J. Ubiquilin at a crossroads in protein degradation pathways. Autophagy. 2010; 6(7).
23. Hernandez F, Diaz-Hernandez M, Avila J, Lucas J J. Testing the ubiquitin-proteasome hypothesis of neurodegeneration in vivo. Trends Neurosci. 2004; 27(2):66-9.
24. Deng H X, Shi Y, Furukawa Y, Zhai H, Fu R, Liu E, et al. Conversion to the amyotrophic lateral sclerosis phenotype is associated with intermolecular linked insoluble aggregates of SOD1 in mitochondria. Proc Natl Acad Sci USA. 2006; 103(18):7142-7.
25. Shibata N, Hirano A, Kobayashi M, Siddique T, Deng H X, Hung W Y, et al. Intense superoxide dismutase-1 immunoreactivity in intracytoplasmic hyaline inclusions of familial amyotrophic lateral sclerosis with posterior column involvement. J Neuropathol Exp Neurol. 1996; 55(4):481-90.
26. Deng H X, Zhai H, Bigio E H, Yan J, Fecto F, Ajroud K, et al. FUS-immunoreactive inclusions are a common feature in sporadic and non-SOD1 familial amyotrophic lateral sclerosis. Ann Neurol. 2010; 67(6):739-48.
27. Mackenzie I R, Bigio E H, Ince P G, Geser F, Neumann M, Cairns N J, et al. Pathological TDP-43 distinguishes sporadic amyotrophic lateral sclerosis from amyotrophic lateral sclerosis with SOD1 mutations. Ann Neurol. 2007; 61(5):427-34.

28. Neumann M, Sampathu D M, Kwong L K, Truax A C, Micsenyi M C, Chou T T, et al. Ubiquitinated TDP-43 in frontotemporal lobar degeneration and amyotrophic lateral sclerosis. Science. 2006; 314(5796):130-3.
29. N'Diaye E N, Hanyaloglu A C, Kajihara K K, Puthenveedu M A, Wu P, von Zastrow M, et al. The ubiquitin-like protein PLIC-2 is a negative regulator of G protein-coupled receptor endocytosis. Mol Biol Cell. 2008; 19(3):1252-60. PMCID: 2262968.
30. Massey L K, Mah A L, Ford D L, Miller J, Liang J, Doong H, et al. Overexpression of ubiquilin decreases ubiquitination and degradation of presenilin proteins. J Alzheimers Dis. 2004; 6(1):79-92.
31. Schrader E K, Harstad K G, Matouschek A. Targeting proteins for degradation. Nat Chem. Biol. 2009; 5(11):815-22.
32. Aguzzi A, O'Connor T. Protein aggregation diseases: pathogenicity and therapeutic perspectives. Nat Rev Drug Discov. 2010; 9(3):237-48.
33. Shimura H, Hattori N, Kubo S, Mizuno Y, Asakawa S, Minoshima S, et al. Familial Parkinson disease gene product, parkin, is a ubiquitin-protein ligase. Nat. Genet. 2000; 25(3):302-5.
34. Leroy E, Boyer R, Auburger G, Leube B, Ulm G, Mezey E, et al. The ubiquitin pathway in Parkinson's disease. Nature. 1998; 395(6701):451-2.
35. Brooks B R, Miller R G, Swash M, Munsat T L. El Escorial revisited: revised criteria for the diagnosis of amyotrophic lateral sclerosis. Amyotroph Lateral Scler Other Motor Neuron Disord. 2000; 1(5):293-9.
36. Neary D, Snowden J S, Gustafson L, Passant U, Stuss D, Black S, et al. Frontotemporal lobar degeneration: a consensus on clinical diagnostic criteria. Neurology. 1998; 51(6):1546-54.

What is claimed is:

1. A method of detecting a mutation in a UBQLN2 nucleic acid in a human sample, comprising:
   (a) contacting a UBQLN2 nucleic acid in a human sample with an oligonucleotide that specifically hybridizes to one or more missense mutations in a UBQLN2 nucleic acid, wherein the one or more missense mutations results in a substitution of a proline in the 12 P-X-X tandem repeats encoded by the UBQLN2 gene; and
   (b) detecting hybridization of the oligonucleotide with the UBQLN2 nucleic acid under specific hybridization conditions, wherein detection of hybridization is indicative of a mutation in the UBQLN2 nucleic acid.

2. The method of claim 1, wherein said human sample comprises a cell, secretion, blood, or fraction thereof.

3. The method of claim 1, wherein the one or more missense mutations are selected from: c.1490C>A, c.1489C>T, c.1516C>A, c.1525C>T, and c.1573C>T[H].

4. A method of detecting a mutation in a UBQLN2 nucleic acid in a human sample, comprising:
   (a) contacting a UBQLN2 nucleic acid in a human sample with an oligonucleotide that specifically hybridizes to one or more missense mutations in a UBQLN2 nucleic acid, wherein the one or more missense mutations is selected from: c.1490C>A, c.1489C>T, c.1516C>A, c.1525C>T, and c.1573C>T; and
   (b) detecting hybridization of the oligonucleotide with the UBQLN2 nucleic acid under specific hybridization conditions, wherein detection of hybridization is indicative of a mutation in the UBQLN2 nucleic acid.

* * * * *

UNITED STATES PATENT AND TRADEMARK OFFICE
CERTIFICATE OF CORRECTION

| | | |
|---|---|---|
| PATENT NO. | : 9,173,897 B2 | Page 1 of 1 |
| APPLICATION NO. | : 13/313884 | |
| DATED | : November 3, 2015 | |
| INVENTOR(S) | : Teepu Siddique et al. | |

It is certified that error appears in the above-identified patent and that said Letters Patent is hereby corrected as shown below:

In the Specification

Insert the following at Column 1, Line 10:
--STATEMENT REGARDING FEDERALLY SPONSORED RESEARCH OR DEVELOPMENT
This invention was made with government support under NS050641 awarded by the National Institutes of Health. The government has certain rights in the invention.--

Signed and Sealed this
Fifth Day of April, 2022

Drew Hirshfeld
*Performing the Functions and Duties of the*
*Under Secretary of Commerce for Intellectual Property and*
*Director of the United States Patent and Trademark Office*